US011318232B2

(12) United States Patent
Ilagan et al.

(10) Patent No.: US 11,318,232 B2
(45) Date of Patent: May 3, 2022

(54) COMPOSITIONS AND METHODS FOR DELIVERING DRUGS TO A VESSEL WALL

(71) Applicant: Interface Biologics, Inc., Toronto (CA)

(72) Inventors: Bernadette Ilagan, Woodbridge (CA); Yulin Wang, North York (CA); Georgios Rizis, Toronto (CA); Bingqing Yang, Mississauga (CA); Wendy Alison Naimark, Toronto (CA)

(73) Assignee: Interface Biologics, Inc., Toronto (CA)

( * ) Notice: Subject to any disclaimer, the term of this patent is extended or adjusted under 35 U.S.C. 154(b) by 0 days.

(21) Appl. No.: 16/797,189

(22) Filed: Feb. 21, 2020

(65) Prior Publication Data
US 2020/0188560 A1 Jun. 18, 2020

Related U.S. Application Data

(63) Continuation of application No. PCT/CA2019/050694, filed on May 22, 2019.

(60) Provisional application No. 62/674,998, filed on May 22, 2018.

(51) Int. Cl.
*A61L 29/08* (2006.01)
*A61L 29/16* (2006.01)
*A61K 31/436* (2006.01)
*C08G 18/48* (2006.01)
*C08G 18/73* (2006.01)

(52) U.S. Cl.
CPC ............. *A61L 29/085* (2013.01); *A61L 29/16* (2013.01); *A61K 31/436* (2013.01); *A61L 2420/06* (2013.01); *C08G 18/4854* (2013.01); *C08G 18/73* (2013.01)

(58) Field of Classification Search
None
See application file for complete search history.

(56) References Cited

U.S. PATENT DOCUMENTS

| 3,929,922 | A | 12/1975 | Wilke et al. |
|---|---|---|---|
| 5,362,718 | A | 11/1994 | Skotnicki et al. |
| 5,665,772 | A | 9/1997 | Cottens et al. |
| 5,868,719 | A | 2/1999 | Tsukernik |
| 5,954,706 | A | 9/1999 | Sahatjian |
| 6,127,507 | A | 10/2000 | Santerre |
| 6,280,411 | B1 | 8/2001 | Lennox |
| 6,770,725 | B2 | 8/2004 | Santerre |
| 6,890,546 | B2 | 5/2005 | Mollison et al. |
| 6,939,320 | B2 | 9/2005 | Lennox |
| 7,226,473 | B2 | 6/2007 | Brar et al. |
| 7,572,245 | B2 | 8/2009 | Herweck et al. |
| 7,655,038 | B2 | 2/2010 | Luthra et al. |
| 7,811,622 | B2 | 10/2010 | Bates et al. |
| 8,172,793 | B2 | 5/2012 | Bates et al. |
| 8,177,743 | B2 | 5/2012 | Lennox |
| 8,257,305 | B2 | 9/2012 | Speck et al. |
| 8,425,459 | B2 | 4/2013 | Wang |
| 8,439,868 | B2 | 5/2013 | Speck et al. |
| 8,673,387 | B2 | 3/2014 | Bates et al. |
| 8,900,603 | B2 | 12/2014 | Esfand et al. |
| RE45,500 | E | 4/2015 | Luthra et al. |
| 9,206,283 | B1 | 12/2015 | Santerre et al. |
| 10,195,311 | B2 | 2/2019 | Esfand et al. |
| 2003/0097120 | A1 | 5/2003 | Santerre |
| 2003/0204238 | A1 | 10/2003 | Tedeschi |
| 2005/0131527 | A1 | 6/2005 | Pathak |
| 2006/0020243 | A1 | 1/2006 | Speck et al. |
| 2006/0229711 | A1 | 10/2006 | Yan et al. |
| 2007/0037891 | A1 | 2/2007 | Esfand et al. |
| 2007/0190103 | A1 | 8/2007 | Hossainy et al. |
| 2008/0021385 | A1 | 1/2008 | Barry et al. |
| 2008/0279911 | A1 | 11/2008 | Sutermeister et al. |
| 2009/0076595 | A1 | 3/2009 | Lindquist et al. |
| 2010/0272774 | A1 | 10/2010 | Chappa et al. |
| 2010/0286608 | A1 | 11/2010 | Tittelbach et al. |
| 2011/0015725 | A1 | 1/2011 | Bates et al. |
| 2011/0091508 | A1 | 4/2011 | Esfand et al. |
| 2011/0104228 | A1 | 5/2011 | Esfand et al. |
| 2011/0295200 | A1 | 12/2011 | Speck et al. |
| 2012/0165786 | A1 | 6/2012 | Chappa et al. |
| 2012/0239001 | A1 | 9/2012 | Barry et al. |
| 2012/0296274 | A1 | 11/2012 | Slager |
| 2013/0013048 | A1 | 1/2013 | Toner et al. |
| 2013/0123695 | A1 | 5/2013 | Hoffmann et al. |
| 2013/0142834 | A1* | 6/2013 | Esfand .................... A61L 31/16 424/400 |
| 2013/0190689 | A1 | 7/2013 | Slager |
| 2013/0245058 | A1 | 9/2013 | Hoffmann et al. |
| 2014/0004253 | A1 | 1/2014 | Ruane |
| 2014/0005541 | A1 | 1/2014 | Bates et al. |
| 2014/0178563 | A1 | 6/2014 | Bates et al. |
| 2014/0207061 | A1 | 7/2014 | Holman et al. |
| 2014/0228751 | A1 | 8/2014 | Speck et al. |
| 2014/0288497 | A1 | 9/2014 | Ewing et al. |
| 2014/0350522 | A1 | 11/2014 | McClain et al. |
| 2015/0045877 | A1 | 2/2015 | Pacetti et al. |
| 2015/0140107 | A1 | 5/2015 | Slager et al. |
| 2015/0190519 | A1 | 7/2015 | Desai et al. |
| 2015/0196690 | A1 | 7/2015 | Stankus et al. |
| 2015/0196692 | A1 | 7/2015 | Toner et al. |
| 2015/0209334 | A1 | 7/2015 | Iyer et al. |
| 2015/0209482 | A1 | 7/2015 | Faucher et al. |
| 2015/0209555 | A1 | 7/2015 | Ruane et al. |
| 2015/0231308 | A1 | 8/2015 | Koullick et al. |
| 2015/0250926 | A1 | 9/2015 | McClain et al. |
| 2015/0283304 | A1 | 10/2015 | Esfand et al. |

(Continued)

FOREIGN PATENT DOCUMENTS

CA 2470524 A1 7/2003
CA 2484269 A1 11/2003

(Continued)

OTHER PUBLICATIONS

Clever et al. (Circulation: Cardiovascular Interventions, 9(4), 1-11, 2016). Novel Sirolimus-Coated Balloon Catheter . . . .*

(Continued)

*Primary Examiner* — Tigabu Kassa
(74) *Attorney, Agent, or Firm* — Clark & Elbing LLP

(57) ABSTRACT

The invention relates to balloon coatings and their use in delivering drugs via a drug-eluting balloon. The delivery can be, e.g., to a vessel wall.

10 Claims, 15 Drawing Sheets

(56) References Cited

U.S. PATENT DOCUMENTS

| | | |
|---|---|---|
| 2018/0028721 A1 | 2/2018 | Esfand et al. |
| 2019/0298889 A1 | 10/2019 | Esfand et al. |

FOREIGN PATENT DOCUMENTS

| | | |
|---|---|---|
| CA | 2555364 A1 | 9/2005 |
| CA | 2673991 A1 | 7/2008 |
| CA | 2793832 A1 | 9/2011 |
| EP | 1087801 B1 | 1/2002 |
| EP | 975340 B1 | 10/2004 |
| EP | 1666071 B1 | 8/2007 |
| EP | 1666070 B1 | 9/2007 |
| EP | 1857127 A1 | 11/2007 |
| EP | 1339440 B1 | 12/2007 |
| EP | 1539266 B1 | 4/2008 |
| EP | 1582210 B1 | 2/2010 |
| EP | 2216055 A1 | 8/2010 |
| EP | 2216056 A1 | 8/2010 |
| EP | 2301619 A1 | 3/2011 |
| EP | 2386322 A2 | 11/2011 |
| EP | 1632259 B1 | 12/2011 |
| EP | 2292225 B1 | 5/2012 |
| EP | 2636416 A2 | 9/2013 |
| EP | 2324866 B1 | 6/2014 |
| EP | 2324867 B1 | 6/2014 |
| EP | 2258415 B1 | 10/2014 |
| EP | 2019698 B1 | 11/2014 |
| EP | 2531229 B1 | 12/2014 |
| EP | 2857048 A1 | 4/2015 |
| EP | 2857049 A1 | 4/2015 |
| JP | 2009-533519 A | 9/2009 |
| WO | WO-02/098477 A2 | 12/2002 |
| WO | WO-2004/028610 A2 | 4/2004 |
| WO | WO-2007/004067 A2 | 1/2007 |
| WO | WO-2007/040557 A1 | 4/2007 |
| WO | WO-2007/148230 A2 | 12/2007 |
| WO | WO-2008/076345 A1 | 6/2008 |
| WO | WO-2009/043174 A1 | 4/2009 |
| WO | WO-2009/049426 A1 | 4/2009 |
| WO | WO-2009/129385 A1 | 10/2009 |
| WO | WO-2010/025398 A1 | 3/2010 |
| WO | WO-2010/111232 A9 | 3/2011 |
| WO | WO-2011/072398 A1 | 6/2011 |
| WO | WO-2011/147408 A2 | 12/2011 |
| WO | WO-2015/070814 A1 | 5/2015 |
| WO | WO-2015/112348 A1 | 7/2015 |

OTHER PUBLICATIONS

International Search Report and Written Opinion for International Application No. PCT/CA2019/050694, dated Jul. 29, 2019 (11 pages).

Benneche et al., "Pyrimidinones as reversible metaphase arresting agents," Eur J Med Chem. 28:463-72(1993).

Gurd, "Carboxymethylation," Methods Enzymol. 11:532-41 (1967).

Herriott, "Reactions of Native Proteins with Chemical Reagents," Adv Protein Chem. 3:169-225 (1947).

Herzig et al., "Bifunctional reagents and protein structure determination. The reaction of phenolic disulfonyl chlorides with lysozyme," Biopolymers. 2:349-60 (1964).

Hunter et al., "The Reaction of Imidoesters with Proteins and Related Small Molecules," J Am Chem Soc. 84(18):3491-3504 (1962).

McAlpine et al., "Revised NMR assignments for rapamycin," J Antibiodics. 44(6):688-90 (1991).

McKenzie et al., "Development of a bifunctional crosslinking agent with potential for the preparation of immunotoxins," J Protein Chem. 7(5):581-92 (1988).

Peppas et al., "New challenges in biomaterials," Science. 263(5154):1715-20 (1994).

Perin, "Choosing a drug-eluting stent: A comparison between CYPHER and TAXUS," Rev Cardiovasc Med. 6( suppl 1):S13-S21 (2005).

Smyth et al., "Some Reactions of N-Ethylmaleimide," J Am Chem Soc. 82(17):4600-04 (1960).

Smyth et al., "Reactions of N-Ethylmaleimide with peptides and amino acids," Biochem J. 91:589-95(1964).

Tietze et al., "Squaric acid diethyl ester: A new coupling reagent for the formation of drug biopolymer conjugates. Synthesis of squaric acid ester amides and diamides," Chem Ber. 124:1215-21 (1991).

Van Duyne et al., "Atomic structure of the rapamycin human immunophilin FKBP-12 complex," J Am Chem Soc. 113(13):7433-34 (1991).

Webb et al., "Synthesis of 1-(aminooxy)-4-[(3-nitro-2-pyridyl)dithio]butane and 1-(aminooxy)-4-[(3-nitro-2-pyridyl)dithio]but-2-ene, novel heterobifunctional cross-linking reagents," Bioconjugate Chem. 1:96-9(1990).

Wetz et al., "Synthesis of 'long,' hydrophilic, protein-cross-linking reagents," Anal Biochem. 58(2):347-60 (1974).

Wong et al., "Uridine diphosphate galactose 4-epimerase. Alkylation of enzyme-bound diphosphopyridine nucleotide by p-(bromoacetamido)phenyl uridyl pyrophosphate, an active-site-directed irreversible inhibitor," Biochem. 18(24):5337-41 (1979).

Allouch et al., "Nonionic amphiphilic compounds from aspartic and glutamic acids as structural mimics of lecithins," JAOCS 73(1):87-96 (1996).

Heimann et al., "Hydrophile fette," Liebigs Ann. Chem. 6:858-62 (1980) (English abstract included).

Waksman et al., "Drug-eluting balloon: the comeback kid?," Circ Cardiovasc Interv. 2(4):352-8 (2009).

Durrieu et al., "Preparation of aqueous anionic poly(urethane-urea) dispersions. Influence of the incorporation of acrylic, polycarbonate and perfluoro-oligoether diols on the dispersion and polymer properties," Polym Adv Technol. 16:840-845 (2005).

Cavanaugh, "Regulatory perspectives for DCB development and approval in the United States," TCT, Oct. 25, Miami, FL. 2012 (19 pages).

Zeller et al., "Drug-eluting balloon versus standard balloon angioplasty for infrapopliteal arterial revascularization in critical limb ischemia," Journal of the American College of Cardiology. 64(15):1568-76 (2014).

"Urgent Field Safety Notice: IN.PACT® Amphirion Drug-Eluting Balloon (DEB)," Medtronic, Inc. (2013) (2 pages).

"<788> Particulate Matter in Injections," Revision Bulletin. 1-3 (2012).

Joner et al., "Comparative assessment of drug-eluting balloons in an advanced porcine model of coronary restenosis," Thromb Haemost. 105(5):864-72 (2011).

Radke et al., "Vascular effects of paclitaxel following drug-eluting balloon angioplasty in a porcine coronary model: the importance of excipients," EuroIntervention. 7(6):730-7 (2011).

"Evaluation of particulates associated with vascular medical devices," Association for the Advancement of Medical Instrumentation, Dec. 13, 2010 (58 pages).

Gray et al., "Drug-coated balloons for the prevention of vascular restenosis," Circulation. 121(24):2672-80 (2010).

Smith, "FDA engineers perspective: drug-coated balloons," CRT, Mar. 6, Washington DC. 2009 (8 pages).

International Preliminary Report on Patentability for International Application No. PCT/CA2019/050694, dated Nov. 24, 2020 (7 pages).

* cited by examiner

FIG. 3
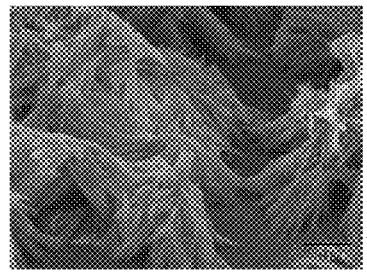
FIG. 4
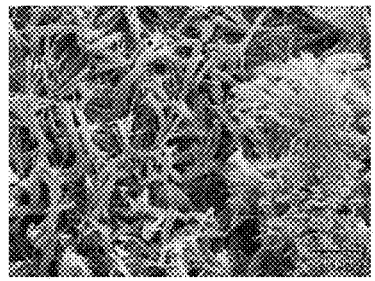
Pebax      Nylon 12
SEM image
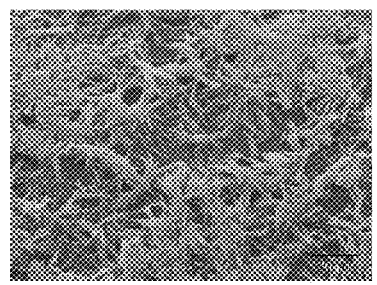  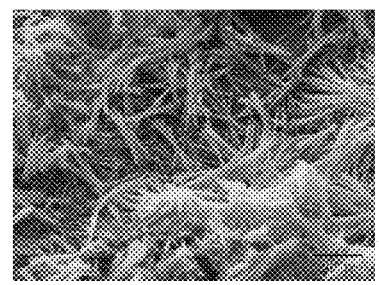
FIG. 5A      FIG. 5B
Optical image
  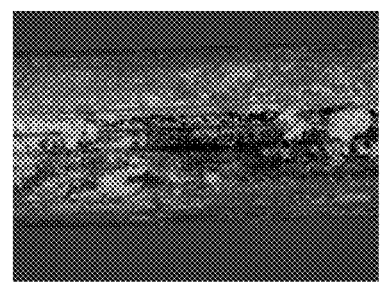
FIG. 5C      FIG. 5D

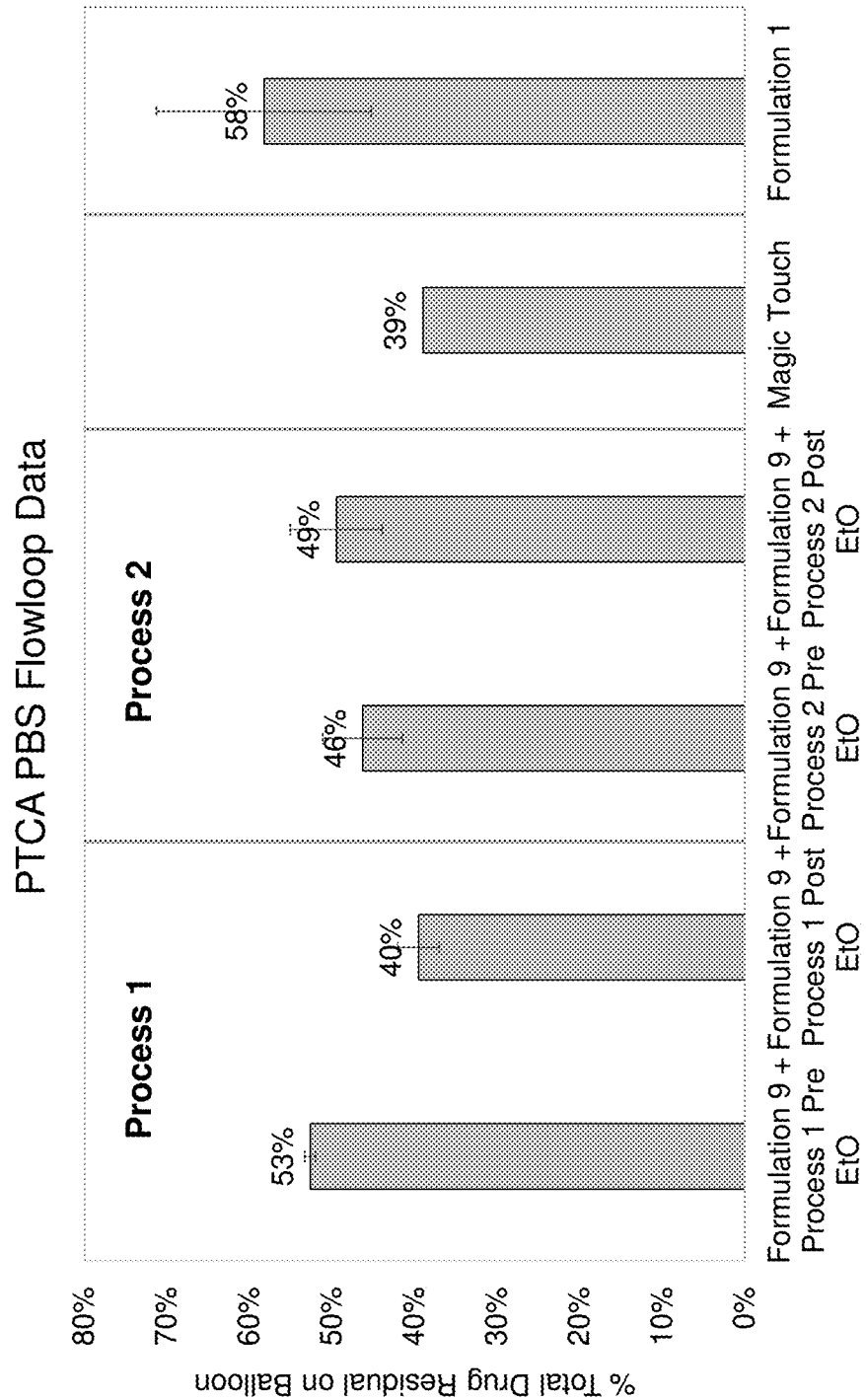

COMPOSITIONS AND METHODS FOR DELIVERING DRUGS TO A VESSEL WALL

RELATED APPLICATIONS

This is a Patent Cooperation Treaty Application which claims the benefit of 35 U.S.C. § 119 based on the priority of U.S. Provisional Application No. 62/674,998, filed May 22, 2018, which is incorporated herein by reference in its entirety.

BACKGROUND OF THE INVENTION

The invention features balloon coatings and their use in delivering drugs to a vessel wall.

The development of coated balloon catheters for delivery of paclitaxel presents a number of technical challenges, including the problem of the transit-associated loss of paclitaxel which can arise in the process of the delivery of paclitaxel to a target site. It is recognized in the art that the dominant design challenge for the success of drug-coated balloon technology is the development of a coating system with properties robust enough to physically maintain the agent on the surface of the balloon during transit of the device through the vascular system but still allow its rapid, uniform, efficient, and directed (i.e., with limited downstream distribution) transference to the vessel wall during balloon inflation (Gray and Granada, *Circulation*, 121:2672-2680 (2010)).

The transit-associated loss of paclitaxel can occur during the passage of a coated balloon catheter from the point of entry into a blood vessel to arrival at the site where, and time when, the balloon is expanded to contact the vessel wall with the paclitaxel coating. The transit-associated loss of paclitaxel is undesirable for two reasons: (i) paclitaxel available at the target site is reduced by the transit-associated loss of paclitaxel, and (ii) paclitaxel is a cytotoxic agent making the systemic release into the blood stream undesirable.

Another technical challenge for the development of coated balloon catheters for delivery of paclitaxel is the problem of potential embolization by paclitaxel-containing particles released during the procedure.

There is a need for improved drug coating techniques to address the challenges of transit-associated loss and potential embolization by drug-containing particles.

SUMMARY OF THE INVENTION

The methods and compositions of the invention feature formulations for coating balloons, and their use in drug delivery.

The invention features a coating including: (i) from 3% to 35% (w/w) of a compound of formula (I)

$$F_T\text{-}[B\text{-}(\text{oligo})]_n\text{-}B\text{-}G_T \quad \quad (I),$$

wherein B is a hard segment formed from hexamethylene diisocyanate, oligo is an oligomeric segment including polytetramethylene oxide, FT is a polyfluoroorgano group, and n is an integer from 1 to 10; and (ii) from 70% to 97% (w/w) crystalline paclitaxel dihydrate. In particular embodiments, the coating includes (i) from 15% to 25% (w/w) of the compound of formula (I) and (ii) from 75% to 85% (w/w) crystalline paclitaxel dihydrate. In some embodiments, the polytetramethylene oxide has a molecular weight of from about 800 Da to 3,000 Da (e.g., from about 800 Da to 2,500 Da, about 800 Da to 2,000 Da, about 800 Da to 1,500 Da).

In some embodiments, the polyfluoroorgano group is a polyfluoroalkyl having a molecular weight of between 100-1,500 Da. In other embodiments, the polyfluoroorgano group is a radical of the general formula $CF_3(CF_2)_rCH_2CH_2\text{---}$ or $CF_3(CF_2)_s(CH_2CH_2O)_x\text{---}$, wherein r is an integer from 2-20, x is an integer from 1-10, and s is an integer from 1-20. In still other embodiments, the polyfluoroorgano group is a radical of the general formula $CH_mF_{(3-m)}(CF_2)_rCH_2CH_2\text{---}$ or $CH_mF_{(3-m)}(CF_2)_s(CH_2CH_2O)_x\text{---}$, wherein m is 0, 1, 2, or 3; x is an integer between 1-10; r is an integer between 2-20; and s is an integer between 1-20. In certain embodiments, the polyfluoroorgano group is selected from $(CF_3)(CF_2)_5CH_2CH_2O\text{---}$, $(CF_3)(CF_2)_7CH_2CH_2O\text{---}$, $(CF_3)(CF_2)_5CH_2CH_2O\text{---}$, $CHF_2(CF_2)_3CH_2O\text{---}$, and $(CF_3)(CF_2)_2CH_2O\text{---}$, 1H,1H, 2H,2H-perfluoro-1-decanol; 1H,1H, 2H, 2H-perfluoro-1-octanol; 1H, 1H, 5H-perfluoro-1-pentanol; and 1H,1H, perfluoro-1-butanol, and mixtures thereof.

In one embodiment of the above coatings, the coating is a coating on at least a portion of a balloon catheter. In some embodiments, the balloon catheter includes an energy generating element (e.g., an element that generates ultrasound, heat, electromagnetic, mechanical, or vibrational energy). In particular embodiments, the balloon catheter includes lithotripsy electrodes for deliverying ultrasonic energy to a vessel wall. In another embodiment, the balloon catheter includes a mechanical energy generating element (e.g., wherein the balloon catheter is capable of scoring and/or cutting).

In another embodiment of the above coatings, the coating includes a paclitaxel concentration of from 1.0 μg/mm² to 6.0 μg/mm² (e.g., 1.5±0.5 μg/mm², 2.5±0.5 μg/mm², 3.0±0.5 μg/mm², 3.5±0.5 μg/mm², 4.0±0.5 μg/mm², 4.5±0.5 μg/mm², 5.0±0.5 μg/mm², or 5.5±0.5 μg/mm²).

The coating can have a thickness of from 0.01 to 250 microns (e.g., from 0.01 to 5 microns, 0.1 to 5 microns, 1 to 5 microns, 1 to 25 microns, 2 to 25 microns, 5 to 50 microns, 5 to 100 microns, 10 to 250 microns, 15 to 50 microns, or 20 to 125 microns). In particular embodiments, the coating can have a glass transition of from −80 to 90° C. (e.g., from −80 to 5° C., −60 to 5° C., −50 to 20° C., −40 to 30° C., −30 to 40° C., −20 to 40° C., or 25 to 90° C.). In still other embodiments, the coating can have a tack of from 1.0 to 200 g (e.g., from 1.0 to 100 g, 1.0 to 50 g, 2.0 to 200 g, 2.0 to 100 g, 2.0 to 50 g, 1.0 to 25 g, 2.0 to 25 g, 3.0 to 75 g, 3.0 to 50 g, 3.0 to 25 g, or 1.0 to 20 g). The coating can have a viscosity of from 0.04 to 130 cps (e.g., from 20 to 130 cps, 50 to 130 cps, 75 to 130 cps, 0.04 to 30 cps, 0.04 to 70 cps, 0.5 to 130 cps, 0.5 to 13 cps, 0.5 to 30 cps, 0.5 to 70 cps, 1 to 130 cps, 1 to 20 cps, 1 to 50 cps, 5 to 25 cps, or 5 to 75 cps). In some embodiments, the coating has a contact angle hysteresis of the surface of from 20-120° (e.g., from 20-60°, 30-70°, 40-80°, 60-90°, 70-100°, 80-110°, 90-120°, 60-120°, or 35-90°).

The coatings of the invention can be formed by a method including the steps of: (x) dissolving the compound of formula (I) and paclitaxel in a mixture of an organic solvent and water to form a solution, (y) depositing the solution onto a surface, and (z) drying the surface to form the coating. The coating can be applied to the surface of the by solid deposition, spray coating, drop and drag coating, printing, or dip coating the surface with the solution. In particular embodiments, the organic solvent includes tetrahydrofuran, ethanol, acetone, heptane, hexane, methanol, ethyl acetate, toluene, isopropanol, or mixtures thereof. The solution can include from 0% to 20% (w/w) water (e.g., 1.0±0.5%, 2.5±1.0%, 5.0±2.0%, 7.0±1.5%, 8.0±2.0%, 12±2%, or 15±5% (w/w) water).

In a related aspect, the invention features a balloon catheter, wherein at least a portion of the surface of the balloon catheter includes a coating of the invention. In some embodiments, the balloon catheter includes an energy generating element (e.g., an element that generates ultrasound, heat, electromagnetic, mechanical, or vibrational energy). In a particular embodiment, the balloon catheter includes an ultrasound generating element (e.g., a lithotripsy electrode). In another embodiment, the balloon catheter includes a mechanical energy generating element (e.g., wherein the balloon catheter is capable of scoring and/or cutting).

In another aspect, the invention features a method of delivering paclitaxel to a vessel surface of a mammal, the method including contacting the vessel surface with a coating of the invention.

The invention further features a method for inhibiting restenosis at a first site of a diseased vessel wall in a mammal in need thereof, the method including: (i) providing a balloon catheter, wherein at least a portion of the surface of the balloon catheter includes a coating of the invention; (ii) inserting the balloon catheter into a vessel of the mammal and delivering the balloon catheter to the first site of the vessel wall; and (iii) expanding the balloon to contact the coating to the first site and delivering the paclitaxel to the vessel wall.

In one particular embodiment, the balloon when expanded in water for 1 minute produces a cumulative count of fewer than 1,500 particles greater than 25 μm in diameter (e.g., fewer than 1,400 particles, 1,300 particles, 1,200 particles, or 1,000 particles greater than 25 μm in diameter). In certain embodiments of the method, in a porcine model from 75% to 95% (w/w) of the paclitaxel is retained on the balloon catheter prior to delivery to the vessel wall. In other embodiments of the method, in a porcine model from 45% to 65% (w/w) of the paclitaxel is retained on the balloon catheter immediately after delivery to the vessel wall.

The method of inhibiting restenosis can further include: (iv) following step (iii) and prior to removing the balloon catheter from the vessel, contracting the size of the balloon; (v) moving the balloon to a second site of the diseased vessel wall; and (vi) expanding the balloon to contact the coating to the second site and delivering the paclitaxel to the vessel wall. The method can further include: (vii) following step (vi) and prior to removing the balloon catheter from the vessel, contracting the size of the balloon; (viii) moving the balloon to a third site of the diseased vessel wall; and (ix) expanding the balloon to contact the coating to the third site and delivering the paclitaxel to the vessel wall.

In a related aspect, the invention features a method for inhibiting restenosis at a first site of a calcified vessel wall in a mammal in need thereof, the method including: (i) providing a lithotripsy balloon catheter including one or more lithotripsy electrodes, wherein at least a portion of the surface of the lithotripsy balloon catheter includes a coating including crystalline paclitaxel dihydrate dispersed in a lipophilic carrier at a concentration of from 1.0 to 6.0 μg/mm² (e.g., 1.5±0.5 μg/mm², 2.5±0.5 μg/mm², 3.0±0.5 μg/mm², 3.5±0.5 μg/mm², 4.0±0.5 μg/mm², 4.5±0.5 μg/mm², 5.0±0.5 μg/mm², or 5.5±0.5 μg/mm² PTX); (ii) inserting the balloon catheter into a vessel of the mammal and delivering the balloon catheter to the first site of the vessel wall; (iii) expanding the balloon to contact the coating to the first site and delivering paclitaxel to the first site of the vessel wall and activating the one or more lithotripsy electrodes to delivery ultrasonic energy to the calcified vessel wall; (iv) contracting the size of the balloon; (v) following step (iv) and prior to removing the balloon catheter from the vessel, moving the balloon to a second site of the calcified vessel wall; and (vi) expanding the balloon to contact the coating to the second site and delivering paclitaxel to the second site of the vessel wall and activating the one or more lithotripsy electrodes to delivery ultrasonic energy to the calcified vessel wall, wherein the lipophilic carrier includes butyryltrihexyl citrate or acetyl tributyl citrate, or the coating is a coating of the invention including a compound of formula (I).

In particular embodiments of the method, the coating includes 50% to 95% (w/w) (e.g., 55±5%, 65±5%, 75±5%, or 85±5% (w/w)) crystalline paclitaxel dihydrate and 5% to 50% (w/w) (e.g., 10±5%, 20±5%, 30±5%, or 40±5% (w/w)) butyryltrihexyl citrate.

In some embodiments of the method, the coating includes 50% to 95% (w/w) (e.g., 55±5%, 65±5%, 75±5%, or 85±5% (w/w)) crystalline paclitaxel dihydrate and 5% to 50% (w/w) (e.g., 10±5%, 20±5%, 30±5%, or 40±5% (w/w)) acetyl tributyl citrate.

In any of the above methods, the vessel can be a coronary vessel, an iliac vessel, or a peripheral vessel. For example, the method can be performed as part of a surgical procedure selected from percutaneous translumenal angioplasty, coronary angioplasty, neurovascular angioplasty, balloon angioplasty for AV fistula and AV graft, or balloon aortic valvuplasty. In some embodiments, the method is performed to inhibit restenosis at the site of an arteriovenous shunt.

The invention features a coating including: (i) from 3% to 35% (w/w) of a compound of formula (I)

$$F_T\text{-}[B\text{-}(\text{oligo})]_n\text{-}B\text{-}F_T \qquad (I),$$

wherein B is a hard segment formed from hexamethylene diisocyanate, oligo is an oligomeric segment including polytetramethylene oxide, FT is a polyfluoroorgano group, and n is an integer from 1 to 10; and (ii) from 70% to 97% (w/w) amorphous or crystalline rapamycin macrolide. In particular embodiments, the coating includes (i) from 5% to 25% (e.g., 15% to 25%) (w/w) of the compound of formula (I) and (ii) from 75% to 95% (e.g., 75% to 85%) (w/w) amorphous or crystalline rapamycin macrolide. In some embodiments, the polytetramethylene oxide has a molecular weight of from about 800 Da to 3,000 Da (e.g., from about 800 Da to 2,500 Da, about 800 Da to 2,000 Da, about 800 Da to 1,500 Da). In one example, the amorphous or crystalline rapamycin macrolide is sirolimus.

In some embodiments, the polyfluoroorgano group is a polyfluoroalkyl having a molecular weight of between 100-1,500 Da. In other embodiments, the polyfluoroorgano group is a radical of the general formula $CF_3(CF_2)_rCH_2CH_2$— or $CF_3(CF_2)_s(CH_2CH_2O)_x$—, wherein r is an integer from 2-20, x is an integer from 1-10, and s is an integer from 1-20. In still other embodiments, the polyfluoroorgano group is a radical of the general formula $CH_mF_{(3-m)}(CF_2)_rCH_2CH_2$— or $CH_mF_{(3-m)}(CF_2)_s(CH_2CH_2O)_x$—, wherein m is 0, 1, 2, or 3; x is an integer between 1-10; r is an integer between 2-20; and s is an integer between 1-20. In certain embodiments, the polyfluoroorgano group is selected from $(CF_3)(CF_2)_5CH_2CH_2O$—, $(CF_3)(CF_2)_7CH_2CH_2O$—, $(CF_3)(CF_2)_5CH_2CH_2O$—, $CHF_2(CF_2)_3CH_2O$—, and $(CF_3)(CF_2)_2CH_2O$—, 1H,1H,2H,2H-perfluoro-1-decanol; 1H,1H,2H,2H-perfluoro-1-octanol; 1H,1H,5H-perfluoro-1-pentanol; and 1H,1H, perfluoro-1-butanol, and mixtures thereof.

In one embodiment of the above coatings, the coating is a coating on at least a portion of a balloon catheter. In some embodiments, the balloon catheter includes an energy generating element (e.g., an element that generates ultrasound, heat, electromagnetic, mechanical, or vibrational energy). In particular embodiments, the balloon catheter includes lithotripsy electrodes for deliverying ultrasonic energy to a vessel wall. In another embodiment, the balloon catheter includes a mechanical energy generating element (e.g., wherein the balloon catheter is capable of scoring and/or cutting).

In another embodiment of the above coatings, the coating includes an amorphous or crystalline rapamycin macrolide concentration of from 1.0 μg/mm² to 10.0 μg/mm² (e.g., 1.5±0.5 μg/mm², 2.5±0.5 μg/mm², 3.0±0.5 μg/mm², 3.5±0.5 μg/mm², 4.0±0.5 μg/mm², 4.5±0.5 μg/mm², 5.0±0.5 μg/mm², 5.5±0.5 μg/mm², 6.0±0.5 μg/mm², 6.5±0.5 μg/mm², 7.0±0.5 μg/mm², 7.5±0.5 μg/mm², 8.0±0.5 μg/mm², 8.5±0.5 μg/mm², 9.0±0.5 μg/mm², or 9.5±0.5 μg/mm²). In some embodiments, the amorphous or crystalline rapamycin macrolide concentration is from 1.0 μg/mm² to 6.0 μg/mm² (e.g., 1.5±0.5 μg/mm², 2.5±0.5 μg/mm², 3.0±0.5 μg/mm², 3.5±0.5 μg/mm², 4.0±0.5 μg/mm², 4.5±0.5 μg/mm², 5.0±0.5 μg/mm², or 5.5±0.5 μg/mm²).

The coating can have a thickness of from 0.01 to 250 microns (e.g., from 0.01 to 5 microns, 0.1 to 5 microns, 1 to 5 microns, 1 to 25 microns, 2 to 25 microns, 5 to 50 microns, 5 to 100 microns, 10 to 250 microns, 15 to 50 microns, or 20 to 125 microns). In particular embodiments, the coating can have a glass transition of from −80 to 90° C. (e.g., from −80 to 5° C., −60 to 5° C., −50 to 20° C., −40 to 30° C., −30 to 40° C., −20 to 40° C., or 25 to 90° C.). In still other embodiments, the coating can have a tack of from 1.0 to 200 g (e.g., from 1.0 to 100 g, 1.0 to 50 g, 2.0 to 200 g, 2.0 to 100 g, 2.0 to 50 g, 1.0 to 25 g, 2.0 to 25 g, 3.0 to 75 g, 3.0 to 50 g, 3.0 to 25 g, or 1.0 to 20 g). The coating can have a viscosity of from 0.04 to 130 cps (e.g., from 20 to 130 cps, 50 to 130 cps, 75 to 130 cps, 0.04 to 30 cps, 0.04 to 70 cps, 0.5 to 130 cps, 0.5 to 13 cps, 0.5 to 30 cps, 0.5 to 70 cps, 1 to 130 cps, 1 to 20 cps, 1 to 50 cps, 5 to 25 cps, or 5 to 75 cps). In some embodiments, the coating has a contact angle hysteresis of the surface of from 20-120° (e.g., from 20-60°, 30-70°, 40-80°, 60-90°, 70-100°, 80-110°, 90-120°, 60-120°, or)35-90°.

The coatings of the invention can be formed by a method including the steps of: (x) dissolving the compound of formula (I) and rapamycin macrolide in a mixture of an organic solvent and water to form a solution, (y) depositing the solution onto a surface, and (z) drying the surface to form the coating. In another example, coatings of the invention can be formed by a method comprising the steps of: (x) dissolving the compound of formula (I) in an organic solvent and adding to crystalline rapamycin macrolide to form a suspension, (y) depositing the suspension onto a surface, and (z) drying the surface to form the coating. In some embodiments, the drying process increases rapamycin macrolide crystallinity prior to sterilization. In further examples, sterilization or exposure to humidity can increase rapamycin macrolide crystalline. The coating can be applied to the surface of the by solid deposition, spray coating, drop and drag coating, printing, or dip coating the surface with the solution.

In particular embodiments, the organic solvent includes methyl tert-butyl ether, tetrahydrofuran, ethanol, acetone, heptane, hexane, methanol, ethyl acetate, toluene, isopropanol, or mixtures thereof. The solution can include from 0% to 20% (w/w) water (e.g., 1.0±0.5%, 2.5±1.0%, 5.0±2.0%, 7.0±1.5%, 8.0±2.0%, 12±2%, or 15±5% (w/w) water).

In a related aspect, the invention features a balloon catheter, wherein at least a portion of the surface of the balloon catheter includes a coating of the invention. In some embodiments, the balloon catheter includes an energy generating element (e.g., an element that generates ultrasound, heat, electromagnetic, mechanical, or vibrational energy). In a particular embodiment, the balloon catheter includes an ultrasound generating element (e.g., a lithotripsy electrode). In another embodiment, the balloon catheter includes a mechanical energy generating element (e.g., wherein the balloon catheter is capable of scoring and/or cutting).

In another aspect, the invention features a method of delivering rapamycin macrolide to a vessel surface of a mammal, the method including contacting the vessel surface with a coating of the invention.

The invention further features a method for inhibiting restenosis at a first site of a diseased vessel wall in a mammal in need thereof, the method including: (i) providing a balloon catheter, wherein at least a portion of the surface of the balloon catheter includes a coating of the invention; (ii) inserting the balloon catheter into a vessel of the mammal and delivering the balloon catheter to the first site of the vessel wall; and (iii) expanding the balloon to contact the coating to the first site and delivering the rapamycin macrolide to the vessel wall.

In one particular embodiment, the balloon when expanded in water for 1 minute produces a cumulative count of fewer than 1,500 particles greater than 25 μm in diameter (e.g., fewer than 1,400 particles, 1,300 particles, 1,200 particles, or 1,000 particles greater than 25 μm in diameter). In certain embodiments of the method, in a porcine model from 75% to 95% (w/w) of the rapamycin macrolide is retained on the balloon catheter prior to delivery to the vessel wall. In other embodiments of the method, in a porcine model from 10% to 65% (w/w) (e.g., 45% to 65% (w/w)) of the rapamycin macrolide is retained on the balloon catheter immediately after delivery to the vessel wall.

The method of inhibiting restenosis can further include: (iv) following step (iii) and prior to removing the balloon catheter from the vessel, contracting the size of the balloon; (v) moving the balloon to a second site of the diseased vessel wall; and (vi) expanding the balloon to contact the coating to the second site and delivering the rapamycin macrolide to the vessel wall. The method can further include: (vii) following step (vi) and prior to removing the balloon catheter from the vessel, contracting the size of the balloon; (viii) moving the balloon to a third site of the diseased vessel wall; and (ix) expanding the balloon to contact the coating to the third site and delivering the rapamycin macrolide to the vessel wall.

In a related aspect, the invention features a method for inhibiting restenosis at a first site of a calcified vessel wall in a mammal in need thereof, the method including: (i) providing a lithotripsy balloon catheter including one or more lithotripsy electrodes, wherein at least a portion of the surface of the lithotripsy balloon catheter includes a coating including crystalline rapamycin macrolide dispersed in a lipophilic carrier at a concentration of from 1.0 μg/mm² to 10.0 μg/mm² (e.g., 1.5±0.5 μg/mm², 2.5±0.5 μg/mm², 3.0±0.5 μg/mm², 3.5±0.5 μg/mm², 4.0±0.5 μg/mm², 4.5±0.5 μg/mm², 5.0±0.5 μg/mm², 5.5±0.5 μg/mm², 6.0±0.5 μg/mm², 6.5±0.5 μg/mm², 7.0±0.5 μg/mm², 7.5±0.5 μg/mm², 8.0±0.5 μg/mm², 8.5±0.5 μg/mm², 9.0±0.5 μg/mm², or 9.5±0.5 μg/mm²); (ii) inserting the balloon catheter into a vessel of the mammal and delivering the balloon catheter to the first site of the vessel wall; (iii) expanding the balloon to contact the coating to the first site and delivering rapamycin macrolide to the first site of the vessel wall and activating the one or more lithotripsy electrodes to delivery ultrasonic energy to the calcified vessel wall; (iv) contracting the size of the balloon; (v)

following step (iv) and prior to removing the balloon catheter from the vessel, moving the balloon to a second site of the calcified vessel wall; and (vi) expanding the balloon to contact the coating to the second site and delivering rapamycin macrolide to the second site of the vessel wall and activating the one or more lithotripsy electrodes to delivery ultrasonic energy to the calcified vessel wall, wherein the lipophilic carrier includes butyryltrihexyl citrate or acetyl tributyl citrate, or the coating is a coating of the invention including a compound of formula (I). In some embodiments, the crystalline rapamycin macrolide is dispersed in the liphophilic carrier at a concentration of from 1.0 µg/mm² to 6.0 µg/mm² (e.g., 1.5±0.5 µg/mm², 2.5±0.5 µg/mm², 3.0±0.5 µg/mm², 3.5±0.5 µg/mm², 4.0±0.5 µg/mm², 4.5±0.5 µg/mm², 5.0±0.5 µg/mm², or 5.5±0.5 µg/mm²).

In particular embodiments of the method, the coating includes 50% to 95% (w/w) (e.g., 55±5%, 65±5%, 75±5%, or 85±5% (w/w)) crystalline rapamycin macrolide and 5% to 50% (w/w) (e.g., 10±5%, 20±5%, 30±5%, or 40±5% (w/w)) butyryltrihexyl citrate.

In some embodiments of the method, the coating includes 50% to 95% (w/w) (e.g., 55±5%, 65±5%, 75±5%, or 85±5% (w/w)) crystalline rapamycin macrolide and 5% to 50% (w/w) (e.g., 10±5%, 20±5%, 30±5%, or 40±5% (w/w)) acetyl tributyl citrate.

In any of the above methods, the vessel can be a coronary vessel, an iliac vessel, or a peripheral vessel. For example, the method can be performed as part of a surgical procedure selected from percutaneous translumenal angioplasty, coronary angioplasty, neurovascular angioplasty, balloon angioplasty for AV fistula and AV graft, or balloon aortic valvuplasty. In some embodiments, the method is performed to inhibit restenosis at the site of an arteriovenous shunt.

In any of the above methods, the rapamycin macrolide can be selected from sirolimus, zotarolimus, everolimus, temsirolimus, ridaforolimus, umirolimus, and biolimus.

The tack of a coating of the invention can be measured, for example, using a TA.XTPlus Texture Analyser (Stable Micro Systems; distributed by Texture Technologies Corp; Scarsdale, N.Y.), which measures tack in "grams of force".

As used herein, "inhibiting restenosis" refers to reducing the re-narrowing of artries following treatment to clear the blockage, such as angioplasty, using a therapy of the invention in comparison to the re-narrowing that would occur following treatment to clear the blockage in the absence of any further therapy to address the risk of restenosis.

As used herein, the term "cumulative count" refers to the numbers of particles produced by a balloon coated with 3.0 µg/mm² PTX using the method described in Example 14.

As used herein, the term "rapamycin macrolide" refers to rapamycin (also referred to as sirolimus) as well as other macrolide structural analogues of rapamycin which are inhibitors of the mTOR cellular signaling pathway, and preferably inhibitors of mTOR itself. Rapamycin macrolides include everolimus (Affinitor; RAD001), temsirolimus (CCI-779), ridaforolimus (previously known as deforolimus; AP23573), umirolimus (Biolimus A9), zotarolimus (ABT-578), novolimus, myolimus, AP23841, KU-0063794, INK-128, EX2044, EX3855, EX7518, AZD08055 and OSI027.

Other features and advantages of the invention will be apparent from the following Detailed Description, the Drawings, and the Claims.

BRIEF DESCRIPTION OF THE DRAWINGS

FIG. 3 is an SEM image of Formulation 1 coated onto balloon as described in Example 11. The image depicts crystals of PTX dihidrate in the coating.

FIG. 4 is an SEM image of Formulation 2 coated onto balloon as described in Example 12. The image depicts crystals of PTX dihidrate in the coating.

FIGS. 5A-5D are SEM and optical images of Formulation 1 on nylon and Pebax balloons prepared as described in Example 13.

FIG. 19 is a graph depicting drug retention for Formulation 9 coated on Nylon 12 PTCA balloon catheter compared to Magic Touch drug-eluting balloon and Formulation 1 coated Nylon 12 PTCA balloon.

DETAILED DESCRIPTION

Figure 1:
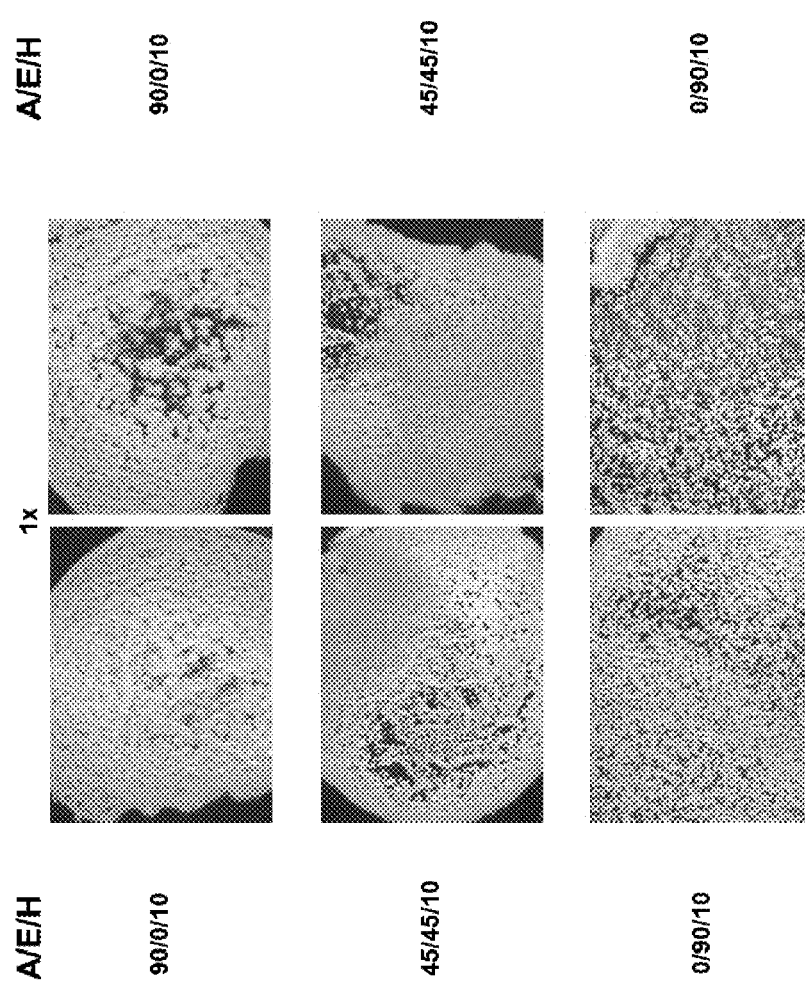
FIG. 1 is an optical image of Formulation 1 (ca. 80% (w/w) crystals of PTX dihidrate dispersed in ca. 20% (w/w) compound 1) coated on nylon coupon formed from different solvent compositions (E=ethanol, A=acetone, and H=water). Formulation 1 was prepared as described in Example 7.

The methods and compositions of the invention feature coatings including a compound of formula (I):

$$F_T-[B-(oligo)]_n-B-F_T \quad (I),$$

wherein B is a hard segment formed from hexamethylene diisocyanate, oligo is an oligomeric segment including polytetramethylene oxide, FT is a polyfluoroorgano group, and n is an integer from 1 to 10; and (ii) crystalline paclitaxel dihydrate or a rapamycin macrolide.

Because the coatings of the invention do not have the properties of a base polymer, they are not susceptible to flaking or cracking during the physical manipulation of the device, such as the expansion and deployment of a balloon catheter. The coatings of the invention can control the release of paclitaxel or rapamycin macrolide incorporated within the coating by limiting the rate of diffusion of the agent from the coating prior to disruption of the coating (e.g., by deformation of the coating, or by exposing the coating to an energy source). A primary function of such coating can be to increase efficacy of local delivery of paclitaxel or a rapamycin macrolide for a defined period of time.

The coatings of the invention can be applied to the surface of a balloon catheter in any number of ways including, but not limited, to electrodeposition, dipping, drag coating, spraying, brushing, printing, or spin coating of the coating material from a solution or suspension followed by solvent removal step as needed. Further description of how the coatings can be made and applied is found in the Examples.

Vascular stenotic/occlusive diseases are mainly caused by changes in pathophysiobiology of the vasculature, resulting in thickening of the vessel lining from fatty deposits or plaques. The most popular mode of therapy for vascular occlusive diseases is the surgical bypass. However, endovascular interventions have been recognized and practiced as an alternative and viable mode of therapy. Balloon angioplasty is designed to expand occluded blood vessels based on balloon inflation, and compression of plaque, allowing perfusion of the diseased tissue. In most endovascular interventions a guiding catheter is advanced in the patient's vasculature until the distal tip of the guiding catheter is located close to the targeted location. A guidewire is advanced out of the distal end of the guiding catheter into the patient's blood vessel, until the distal end of the guidewire crosses a lesion to be dilated. A dilation catheter having an inflatable balloon on the distal portion thereof is advanced into the patient's blood vessel over previously introduced guidewire until the balloon of the dilatation catheter is properly positioned across the lesion. The success of the endovascular intervention is generally high, but the vessel patency is often reduced due to restenosis in the vicinity of the original lesion causing re-occlusion of the vessel. The ability to locally deliver pharmaceuticals from a balloon surface provides an approach in controlling restenosis. The entire or partial external balloon surface can be coated with a desired pharmaceutical, the time of balloon inflation or the multiplicity of inflation can also be controlled, making the "drug eluting balloon" an adaptable and robust tool for local drug delivery.

The compositions and methods of this invention can be used in various applications of drug eluting balloon technology, such as percutaneous translumenal angioplasty (PTA), coronary angioplasty (PTCA), neurovascular angioplasty (PTNA), balloon aortic valvuplasty (BAV). Furthermore, the composition of the invention allows incorporation of various biological agents depending on the application of the drug eluting balloons.

In one application, DEB can also be used as balloon aortic valvuplasty to repair stenotic aortic valve which has become stiff from calcium buildup. The balloon is inserted and inflated into the aortic valve to increase the opening size of the valve and improving blood flow. Traditional balloon aortic valvuloplasty many times fails to prevent restenosis in patients. Drug eluting balloon in this case allows the incorporated antirestenotic drug to elute into dilated aortic valves to prevent restenosis post-treatment.

In another application, DEB can be used to treat coronary and peripheral diseases which are not treatable by stenting. This is particularly true for vessels below the knee in which the vessels are small and the stent struts break under the torque. Additionally, DEB may be used to treat in-stent restenosis. In another example, DEB can be used to treat coronary and peripheral diseases in combination with a stent.

One possible non-vascular application of drug eluting balloon is localized chemotherapy. Balloon catheter can be coated with anticancer agent and introduced to cancerous tissue. A drug eluting balloon may also be used in the nasal cavity and can be used for treating, e.g., chronic sinusitis, such as by coating the DEB with a rapamycin macrolide.

Balloons for angioplasty are categorized as high pressure balloons. A standard balloon consists of a cylindrical body, two conical tapers, and two necks. The particular angles and shapes of the balloon can be customized depending on the application and particularities of the physiology. High pressure balloons are also used to dilate constrictions and blockages in other areas such as the esophagus, biliary-duct, urethra, fallopian-tube, heart-valve, tear-duct and carpel-tunnel dilation. Other applications for high pressure balloons include positioning, occlusion, light therapy, heat transfer and endovascular graft delivery.

High pressure balloons are made from noncompliant or low-compliant materials (expand only 5-10%) which have controllable size and shape. Thin-walled, these balloons exhibit high tensile strength with relatively low elongation. Currently most high pressure balloons are made from PET or nylon. PET has high tensile strength with a maximum pressure rating. It can be molded to have ultra thin walls (5-50 mm) with diameters from 0.5-50 mm. Nylon is softer and can be easily refolded for easier withdrawal into the guiding catheter. Both materials have demonstrated compatibility to coatings which provide lubricity, abrasion and puncture resistance, conductivity, thrombogenicity, drug release, and reflectivity, among other characteristics.

The rated pressure for angioplasty is 2-20 atm. Larger diameter balloons have a lower rated pressure as the stress in the balloon wall increases when inflated to the nominal diameter. PTCA balloon catheters are usually 2-4 mm in diameter, 10-40 mm in length and have a rate pressure of 10-20 atm. PTA balloon catheters are usually 4-14 mm in diameter and 20-200 mm in length and have a rate pressure of 8-20 atm.

A wide variety of balloon catheters can be coated using the compositions and methods of the invention to deliver paclitaxel or a rapamycin macrolide at a desired site of treatment. The balloon catheters of the invention can include energy sources including ultrasound, heat, electromagnetic, mechanical, and/or vibrational energy sources for disrupting the coating and releasing the paclitaxel or a rapamycin macrolide. For example, an ultrasound external energy source may be used having a frequency in a range from 20 kHz to 100 MHz, preferably in a range from 0.1 MHz to 20 MHz, and an intensity level in a range from 0.05 W/cm² to 10 W/cm², preferably in a range from 0.5 W/cm² to 5 W/cm². The ultrasound energy would be directed at the coating and either continuously applied or pulsed, for a time period in a range from 5 seconds to 10 minutes, preferably in a range from 1 minute to 3 minutes. Alternatively, the temperature of the surface of the balloon catheter can be heated (e.g., in the range of from 36° C. to 48° C.), vibrated, or subjected to electromagnetic energy to facilitate the release of paclitaxel or a rapamycin macrolide at the desired place and time. In another example, the balloon catheter includes razor blades, struts, or pull wires that are capable of scoring and/or cutting.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Synthesis and Characterization of Compound 1

To dry reactor glassware was added 1 molar ratio of degassed polytetramethylene oxide diol (M 1000) and dimethyl acetamide (DMAC). To the solution was added 2 molar ratio of hexamethylene diisocyanate, and the reaction flask was placed in a water bath. 0.5 mL of dibutyltin dilaurate (DBTDL) was added to the system. The reaction mixture was stirred for 4 hours at 65° C. to produce the desired HDI PTMO prepolymer. Once the prepolymer reaction is complete, the reactor contents were cooled to 45° C. and degassed FOH C8 was added to the reactor at a molar ratio of 2.3 to end-cap the prepolymer. A Syringe was used to add ca 1.0 mL dibutyltin dilaurate (DBTDL). The reaction mixture was stirred over night at 45° C. to produce the desired fluorinated polymers. The polymer was precipitated in deionized water under constant stirring. The Volume of water used for the precipitation should be approximately 3.3 times the volume of the DMAc solvent in the solution. The polymer was purified by dissolution in boiling isopropanol, followed by cooling to 50-60° C., and precipitation by slow addition of hexane. The precipitated polymer was collected on a filter and washed with hexane. The purified polymer was dried in a convection oven at 50° C. for at least 48 hours to produce compound 1 (general formula depicted below).

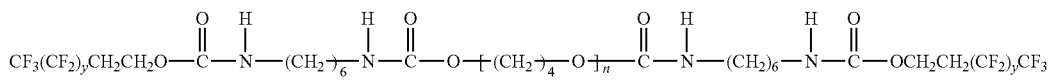

EXAMPLE 2

Synthesis and Characterization of Compound 2

MePEG (15.0 g, 20 mmol) was degassed and then dissolved in DMAc (243 mL), and added dropwise into LDI-methyl (8.48 g, 40 mmol) in DMAc (49 mL) in the presence of DBDL catalyst, at 40° C. over 3 hours under $N_2$. Perfluoroalcohol (24.024 g, 66 mmol) was degased and added to the reaction with present of DBDL catalyst, and stirred at room temperature overnight under $N_2$. The product was purified by cationic SPE and solvent extraction (Compound 2) (general formula depicted below). GPC (THF mobile phase): retention time of 26 minutes, Mw=1921 g/mol, PDI=1.1. HPLC-ELSD analysis: MePEG:LDI-methyl:BAL content 76.9%, MePEG:LDI-methyl:MePEG content 23.1%. 1H NMR (400 MHz, $CDCl_3$) δ (ppm) 4.14-4.27 (—$CH_2$—O, BAL), 4.27-4.45 (—$CH_2$—O—CO, MePEG), 3.72-3.77 (CH3, LDI-methyl), 3.58-3.70 ($CH_2$—$CH_2$—O, MePEG), 3.07-3.22 (CH2-NH, LDI-methyl), 2.35-2.55 (—CH2-CF2-, BAL), 1.22-1.90 (LDI-methyl CH2). Elemental analysis: 12.7% F, 46.7% C, 7.2% H, 2.1% N, <4 ppm Tin. DSC analysis: Tg=−59° C. TGA analysis: Tdeg=275° C.

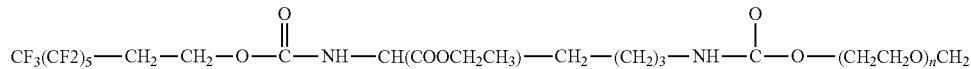

EXAMPLE 3

Sterilization of Compound 1 and Balloon Catheter

Compound 1 from Example 1 was weighed into polypropylene conical tubes capped with lint-free tissue, placed in sterilization pouches, and were sterilized by EtO. The sterilized compositions were analyzed by GPC, NMR and DSC. Results were compared to the pre-sterilization profile. No changes were observed for pre and post sterilization sample.

Balloon catheters coated with Compound 1+ PTX (paclitaxel) dihydrate crystals were also sterilized by EtO. Sterilized and non-sterilized balloon catheters were analyzed by HPLC, and PTX retention time pre and post sterilization compared. PTX HPLC retention time (min): Pre-sterilization: 11.165 (PTX control: 11.163), post sterilization: 10.84 (PTX control: 10.84). Visually, coatings were similar pre and post sterilization with no additional features noted.

EXAMPLE 4

Acute Systemic Toxicity

A single-dose systemic injection of Compound 1 in PBS (5.8 mg/kg) was given to 5 Albino Swiss mice and toxicity observed over a 72 hour period. Mice were dosed at 50 mL/kg at an injection rate of ~0.1 mL/sec. Observations for mortality and signs of pharmacological and/or toxicological effects were made immediately post-injection and at 4, 24, 48 and 72 hours post-injection. No clinical signs of toxicity were observed during the study period.

EXAMPLE 5

Cytotoxicity

Compound 1 was prepared using an extraction ratio of 6 cm$^2$/1 mL 31.6 cm$^2$ of test article was extracted in 5.3 mL of Eagle's minimum essential medium (E-MEM)+5% fetal bovine serum (FBS). Samples were extracted at 37±1° C. for 24±2 hours. The extract was inoculated onto the cell line and incubated at 37±1° C. in a humidified atmosphere with 5±1% $CO_2$ in the air. Positive and negative controls were run in parallel with the test article. Cultures were evaluated for cytotoxic effects by microscopic observation after 24, 48 and 72 hour incubation periods. The test article passes and is considered non-cytotoxic under the test conditions employed.

EXAMPLE 6

Preparation of Compound 1+PTX and Characterization

Compound 1 and PTX (range from 50:50 to 5:95) were dissolved in varying ratios of acetone:ethanol (0:100 to 100:0) with varying water content (0-20%) and used immediately. The presence of PTX dihydrate drug polymorph was confirmed by DSC analysis of material obtained after evaporation of the solvents: Tm=146° C. (the Tm observed for PTX dihydrate alone).

EXAMPLE 7

Preparation of Formulation 1

Compound 1 and PTX were dissolved at 20:80 w/w ratio in acetone:ethanol (0:100 to 100:0 v/v ratio) solution with water and used immediately. Solutions were drop casted onto Nylon 12 coupons and visually inspected (see FIG. 1). The resulting coating, Formulation 1, contains ca. 80% (w/w) crystals of PTX dihydrate dispersed in ca. 20% (w/w) compound 1.

EXAMPLE 8

Preparation of Formulation 2

Figure 2:
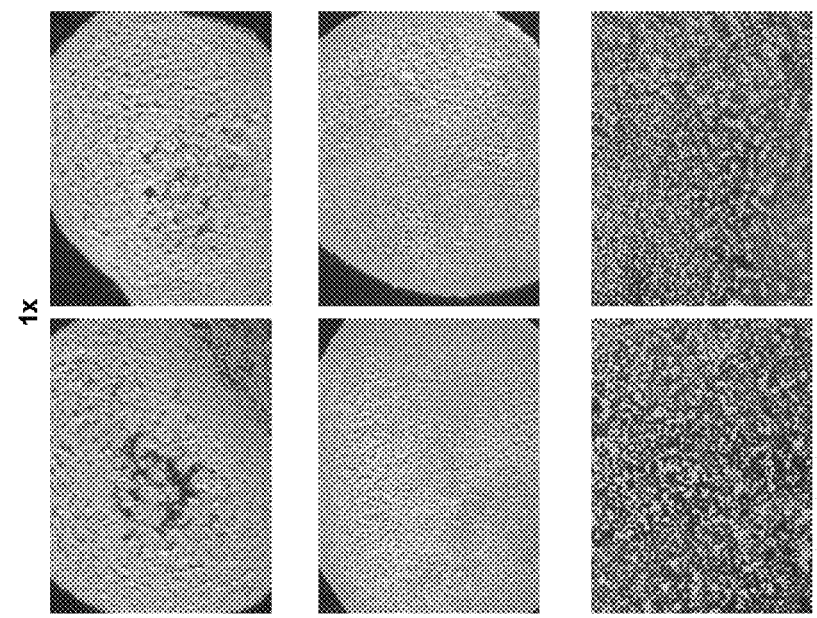
FIG. 2 is an optical image of Formulation 2 (ca. 95% (w/w) crystals of PTX dihidrate dispersed in ca. 5% (w/w) compound 1) coated on nylon coupon formed from different solvent compositions (E=ethanol, A=acetone, and H=water). Formulation 2 was prepared as described in Example 8.

Compound 1 and PTX were dissolved at 5:95 w/w ratio in acetone:ethanol (0:100 to 100:0 v/v ratio) with water and used immediately. Solutions were drop casted onto Nylon 12 coupons and visually inspected (see FIG. 2). The resulting coating, Formulation 2, contains ca. 95% (w/w) crystals of PTX dihydrate dispersed in ca. 5% (w/w) compound 1.

EXAMPLE 9

Preparation of Formulation 3

Compound 1 and PTX were dissolved at 20:80 w/w ratio in tetrahydrofuran and used immediately. Solutions were drop casted onto Nylon 12 coupons and visually inspected. The resulting coating, Formulation 3, contains ca. 80% (w/w) amorphous of PTX dispersed in ca. 20% (w/w) Compound 1.

EXAMPLE 10

Preparation of Formulation 4

Compound 2 and PTX were dissolved at 70:30 w/w ratio in tetrahydrofuran and used immediately. Solutions were drop casted onto Nylon 12 coupons and visually inspected. The resulting coating, Formulation 4, contains ca. 30% (w/w) amorphous of PTX dissolved in ca. 70% (w/w) Compound 2.

EXAMPLE 11

Balloon Coating of Formulation 1 and Characterization

Compound 1 and PTX were dissolved in 1:1 acetone:ethanol with 5% (w/w) water and the resulting solution was immediately coated onto 5.0×40 mm Nylon 12 percutaneous translumenal angioplasty (PTA) balloon catheters by an drop and drag coater and dried overnight to form a coating containing 3.0 μg/mm$^2$ PTX. SEM images of all coated balloons displayed crystalline drug coatings (see FIG. 3).

EXAMPLE 12

Balloon Coating of Formulation 2 and Characterization

Formulation 2 was dissolved in 1:1 acetone:ethanol with 5% (w/w) water and the resulting solution was immediately coated onto 5.0×40 mm Nylon 12 PTA balloon catheters by an in-house drop and drag coater and dried overnight to form a coating containing 3.0 μg/mm$^2$ PTX. SEM images of all coated balloons displayed crystalline drug coatings (see FIG. 4).

EXAMPLE 13

Balloon Coating of Formulation 1 on Different Balloon Platforms

Formulation 1 was coated on Nylon 12 and Pebax based PTA balloon catheters using established drop and drag coating methods. Optical microscopy and SEM showed similar coating morphology with crystalline drug coatings on both Nylon 12 and Pebax balloons (see FIGS. 5A-5D).

EXAMPLE 14

Particle Size Analysis

A suitable apparatus was used based on the principle of lightblockage that allows for an automatic determination of the size of particles and the number of particles according to size. The apparatus is calibrated using dispersions of spherical particles of known sizes between 10 mm and 25 mm. These standard particles were dispersed in particle-free water. Care was taken to avoid aggregation of particles during dispersion.

Particle Size Analysis for Formulation 1

Formulation 1 was coated on Nylon 12 and Pebax balloon catheters to form a coating containing 3 μg/mm² paclitaxel. Coated balloon catheters were exposed to water in a beaker to nominal pressure and held for 1 minute. Water after inflation was analyzed by the particle counter APSS-2000, <788> as a general guideline. The cumulative number of particles were measured for (i) Formulation 1 on a 5×60 mm Nylon 12 balloon catheter (>10 μm: 5117, >25 μm: 664) and (ii) for Formulation 1 on a 5×60 mm Pebax balloon catheter (>10 μm: 3146, >25 μm: 371).

Particle Size Analysis for Formulation 3

Formulation 3 was coated on 5×60 mm Nylon 12 balloon catheters to form a coating containing 3 μg/mm² paclitaxel. Coated balloon catheters were exposed to water in a beaker to nominal pressure and held for 1 minute. Water after inflation was analyzed by the particle counter APSS-2000, <788> as a general guideline.

The cumulative number of particles were measured for Formulation 3 on a Nylon 12 balloon catheter (>10 μm: 2204, >25 μm: 419).

Particle Size Analysis Conclusions

Figure 6:
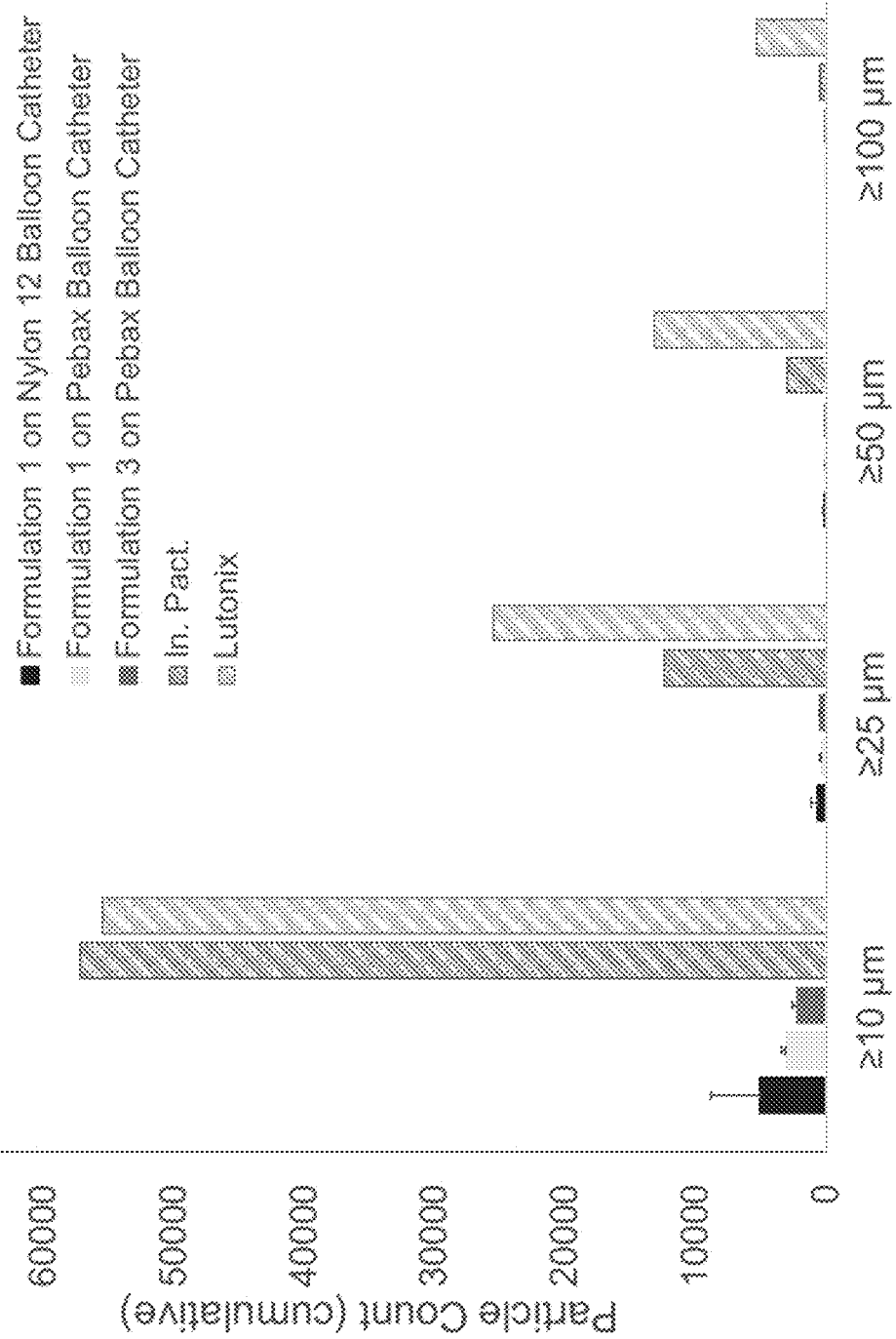
FIG. 6 is a graph depicting the cumulative number of particles formed from balloons bearing different PTX coatings following exposure to water in a beaker as described in Example 14. The following coatings were tested: (a) Formulation 1 coated onto a Nylon 12 balloon catheter; (b) Formulation 1 coated onto a Pebax balloon catheter; (c) IN.PACT™ Admiral™ drug coated balloon catheter; and (d) Lutonix® 035 drug coated balloon PTA catheter. The coatings made from Formulaion 1 exhibit a dramatic reduction in particle counts compared to the IN.PACT™ Admiral™ and Lutonix® 035 balloons.

The particle counts observed for Formulation 1 coated on Nylon 12 and Pebax balloon catheters was significantly lower than the particle counts of 6×60 mm IN.PACT™ Admiral™ drug coated balloon (>10 μm: 57213, >25 μm: 12381), and 6×60 mm Lutonix® 035 drug coated balloon PTA catheter (>10 μm: 55456, >25 μm: 25438) (see FIG. 6). The coatings made from Formulaion 1 exhibit a dramatic reduction in particle counts compared to the IN.PACT® Admiral™ and Lutonix® 035 balloons. The presence of crystalline PTX in Formulation 1 did not significantly impact particle counts relative to the non-crystalline PTX coating of Formulation 3.

EXAMPLE 15

Assessment of Therapeutic Retention of Balloon Coating Under Flow Conditions (Flow Loop Model)

Phosphate buffered saline at 37° C. was pumped by a peristaltic pump through silicone tubing connections. The pump flow rate was set similar to the rate of blood flow through femoral arteries (350 mL/min). A Nylon 12 PTA balloon catheter coated with Formulation 1 was placed in the middle of the buffer flow for 2 minutes. The PTX remaining on the balloon catheter was measured by stripping the coating and quantified using RP-HPLC with benzonitrile as the internal standard. The % PTX remaining was observed to be 95.7%.

Formulation 2 was tested under the same conditions and the % PTX remaining was observed to be 58%.

The high retention of PTX observed for Formulation 1 is consistent with very little PTX lost prior to deployment of the balloon at the treatment site.

EXAMPLE 16

Assessment of Post Treatment Retention of Balloon Coating Under Flow Conditions (Flow Loop Model)

Figure 7:
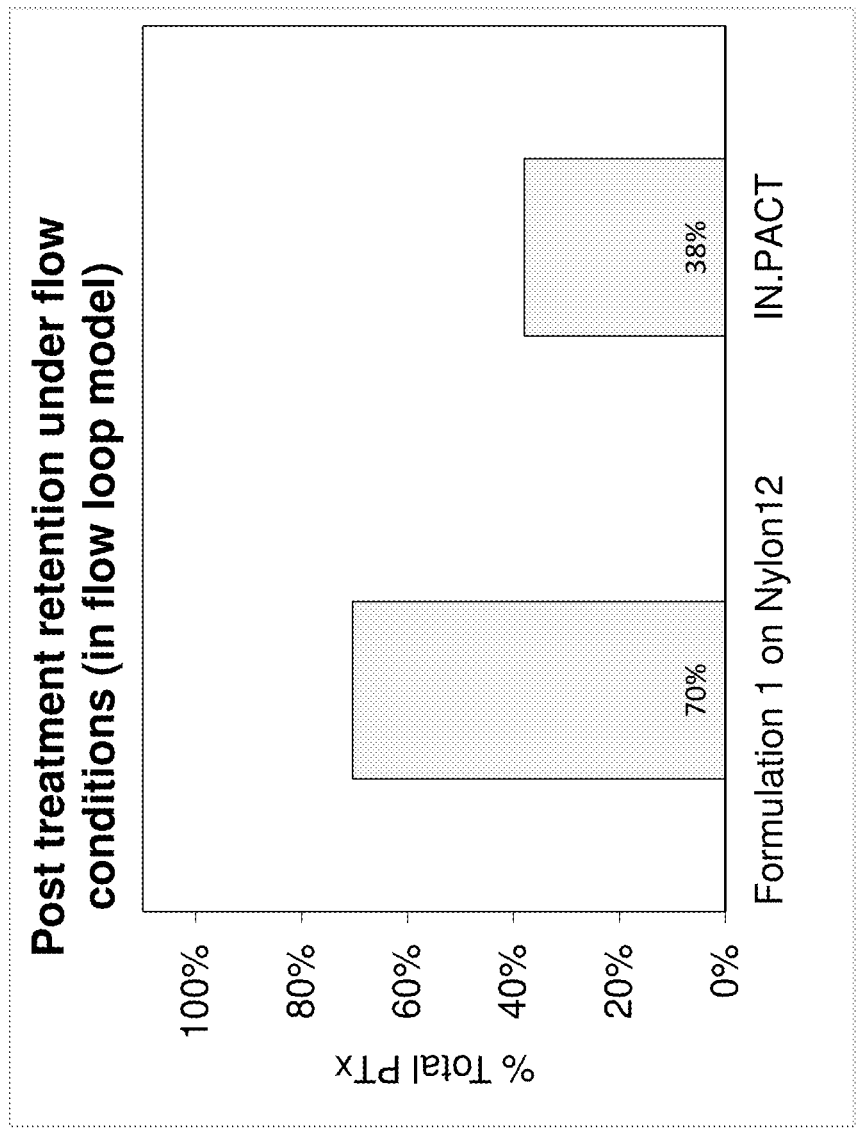
FIG. 7 is a graph depicting the post treatment PTX retention for different balloon coatings in a flow loop model as described in Example 16.

Phosphate buffered saline at 37° C. was pumped by a peristaltic pump through silicone tubing connections. The pump flow rate was set similar to the rate of blood flow through femoral arteries (350 mL/min). A Nylon 12 PTA balloon catheter coated with Formulation 1 was tracked through the silicone tubing under flow, then inflated to establish contact with the silicone tubing. Once inflated, the balloon was held in place for 1 minute, then deflated and removed from the tubing. PTX remaining on the balloon was measured by stripping the coating and quantified using RP-HPLC with benzonitrile as the internal standard. The % PTX remaining was observed to be 70.4%. The amount of PTX remaining on the balloon coated with Formulation 1 was higher than that of the IN.PACT™ model (in house proxy, the % PTX remaining was observed to be 38%—see FIG. 7). The high retention of PTX observed for Formulation 1 post balloon deployment suggest that deployment of the balloon at the treatment site does not compromise the the ability of Formulation 1 to resist loss of PTX after a treatment event.

EXAMPLE 17

Modulating Coating Retention On Balloon Surface After Shockwave Treatment (Flow Loop Model)

Phosphate buffered saline at 37° C. was pumped by a peristaltic pump through silicone tubing connections. The pump flow rate was set similar to the rate of blood flow through femoral arteries (350 mL/min). A Nylon 12 PTA balloon catheter coated with Formulation 1 was tracked through the silicone tubing under flow, then inflated to establish contact with the silicone tubing. Once inflated, the PTA balloon was held in place for 1 minute, then deflated, tracked to a second location and inflated to establish contact with the silicone tubing; the two locations were non-overlapping. The balloon was held inflated in the second position for 1 minute, then deflated and removed from the tubing. PTX remaining on the Nylon 12 PTA balloon was measured by stripping the coating and quantified using RP-HPLC with benzonitrile as the internal standard. The % PTX retention was 59%.

Figure 8:
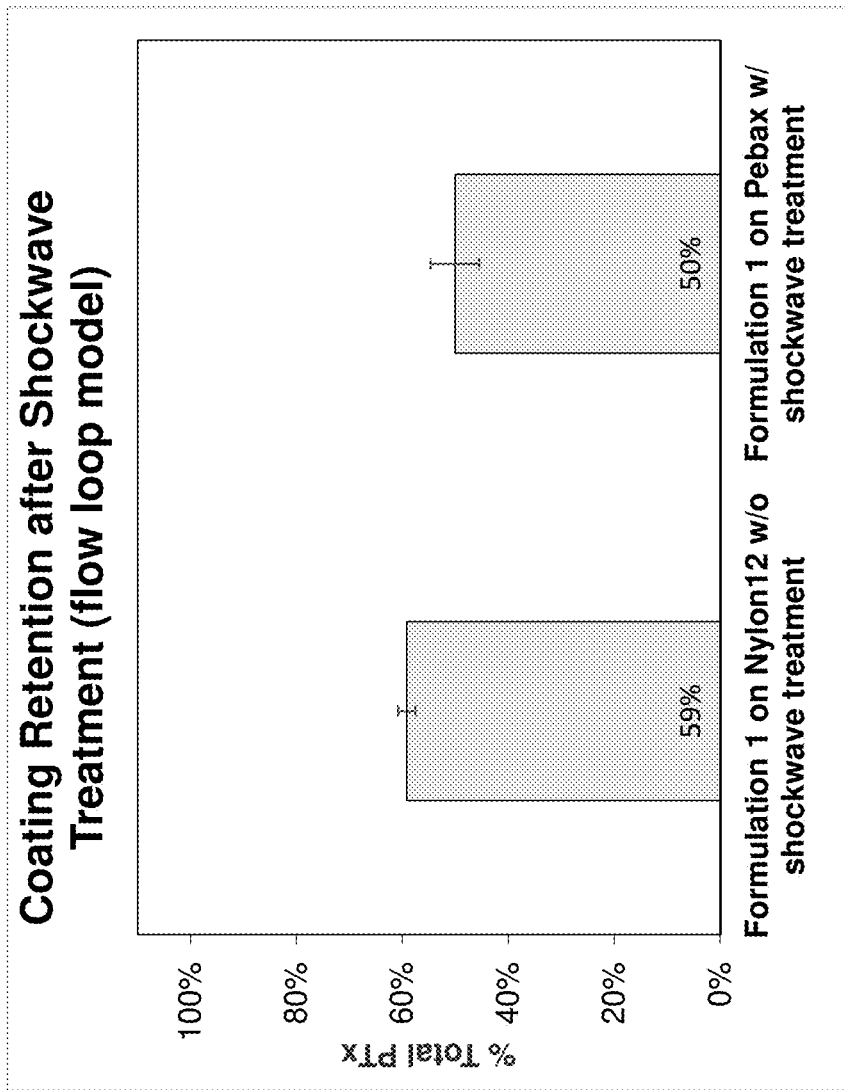
FIG. 8 is a graph depicting the post single treatment with shockwave PTX retention for different balloon coatings in a flow loop model as described in Example 17.

In the same flow loop model, a Pebax PTA lithotripsy catheter coated with Formulation 1 was tracked through the silicone tubing under flow, then inflated to establish contact with the silicone tubing. Once inflated, a mock lithotripsy treatment was initiated, consisting of an acoustic shock sequence with a 1 minute duration. At the end of the shock sequence, the PTA balloon was deflated, tracked to a second location and inflated to establish contact with the silicone tubing, at which point a second 1 minute-long mock lithotripsy treatment was performed; the two locations were non-overlapping. At the end of the second shock sequence, the PTA balloon was deflated and removed from the tubing. PTX remaining on the Pebax PTA balloon was measured by stripping the coating and quantified using RP-HPLC with benzonitrile as the internal standard. The % PTX retention was 50%. The retention of the Formulation 1 on the balloon catheter is not impacted by the lithotripsy treatment (FIG. 8).

EXAMPLE 18

Assessment of Therapeutic Retention of Balloon Coating in a Porcine Model

Figure 9:
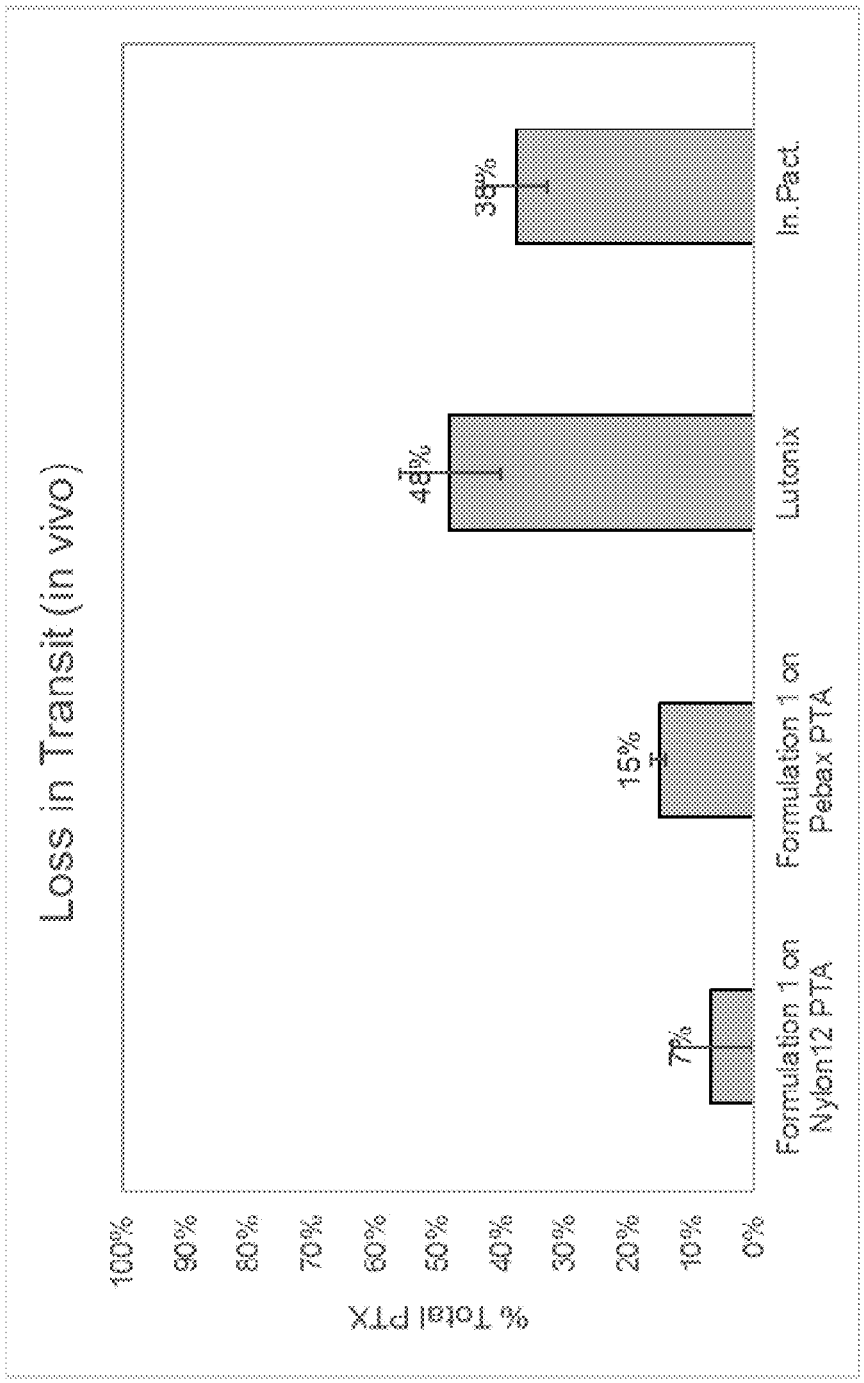
FIG. 9 is a graph depicting the pre-deployment PTX loss in transit for different balloon coatings in a porcine model as described in Example 18.

Balloon catheters coated with Formulation 1 were tracked and placed at the site of inflation in porcine femoral arteries (female farm pigs, Sus scrofa domestica), without inflation, for 1 minute, and withdraw from the animal. Each animal was given ASA (0.081 g) and Clopidogrel (0.075 g) by mouth daily for three days prior to treatment, and was fasted overnight before the procedure. For surgical procedures, after sedation a marginal ear vein was cannulated for infusion of intravenous fluids and medications. The animal was intubated for administration of anesthetic gases and placed on the catheterization table. Under sterile conditions, a vascular introducer sheath was placed in the right carotid artery by surgical cut down. Continuous hemodynamic and electrocardiographic monitoring was maintained throughout the procedure. Using the guide catheter and or marker guidwire as a calibration reference, the diameter of the vessel at reference sites proximal and distal to the intended site of implant, as well as the target site diameter, was measured. The remaining coating on the balloon catheter after the procedure was extracted with appropriate solvent and PTX quanitified by RP-HPLC with benzonitrile as the internal standard. The % PTX released from wrapped balloons was 7% for the Nylon 12 platform, and 15% for the Pebax platform. These values are lower than those of Lutonix® and IN.PACT™ models, which were 48% and 38%, respectively (see FIG. 9).

EXAMPLE 19

Assessment of Post Treatment Retention of Balloon Coating in a Porcine Model

Figure 10:
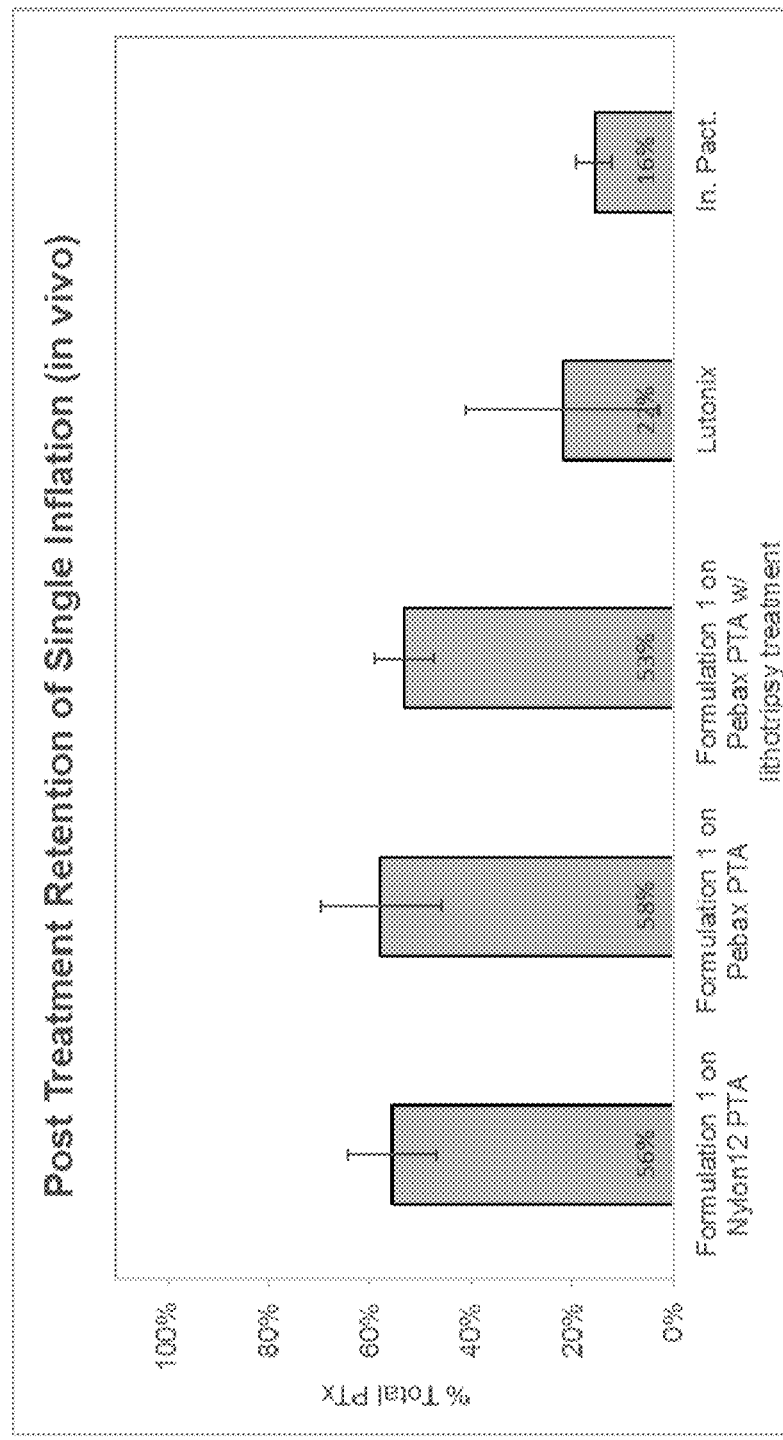
FIG. 10 is a graph depicting the post-deployment (post-inflation) PTX loss for different balloon coatings in a porcine model as described in Example 19.

Nylon 12, Pebax, and Pebax with shockwave balloon catheter coated with Formulation 1 were tracked and placed at the site of inflation in porcine femoral arteries (female farm pigs, Sus scrofa domestica), and inflated to a balloon-to-artery diameter ratio of ~1.20. The nylon 12 and Pebax balloon were inflated and held at the treatment location of 1 minute for drug transfer, then withdrawn from the animal. The Pebax with shockwave balloon catheter were inflated, and a simulated lithotripsy treatment consisting of a 1 minute-long acoustic shock sequence were performed during the drug transfer period, then the balloon is withdrawn from the animal. Each animal was given ASA (0.081 g) and Clopidogrel (0.075 g) by mouth daily for three days prior to treatment, and was fasted overnight before the procedure. For surgical procedures, after sedation a marginal ear vein was cannulated for infusion of intravenous fluids and medications. The animal was intubated for administration of anesthetic gases and placed on the catheterization table. Under sterile conditions, a vascular introducer sheath was placed in the right carotid artery by surgical cut down. Continuous hemodynamic and electrocardiographic monitoring was maintained throughout the procedure. Using the guide catheter and or the marker guidewire as a calibration reference, the diameter of the vessel at reference sites proximal and distal to the intended site of implant, as well as the target site diameter, was measured. The remaining coating on the balloon catheter after the procedure was extracted with appropriate solvent and PTX quanitified by RP-HPLC with benzonitrile as the internal standard. The % PTX remaining on the balloons was 56% for the Nylon 12 balloon, and 58% for the Pebax balloon; the corresponding value for the Pebax balloon used in simulated lithotripsy was 53%. These values are higher than those of Lutonix® and IN.PACT™ models, which were 22% and 16%, respectively (see FIG. 10). Further, the Shockwave lithotripsy treatment showed a minimal impact on drug retention on the device in a porcine model.

EXAMPLE 20

Figure 11:
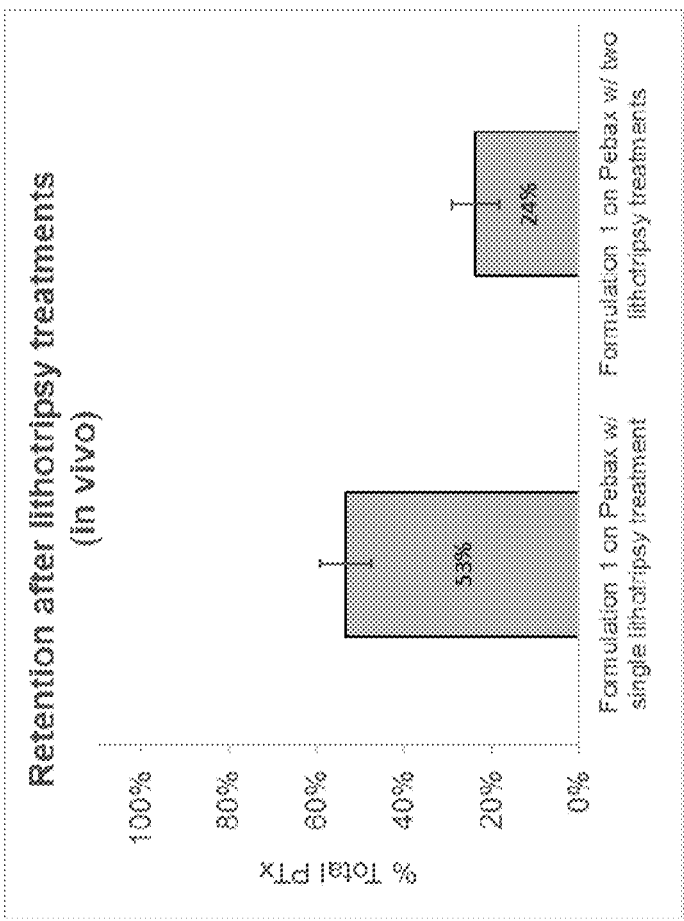
FIG. 11 is a graph depicting the PTX retention for Formulation 1 post multiple inflation and lithotripsy treatments in a porcine model as described in Example 20.

Modulating Coating Retention on Balloon Surface After Multiple Shockwave Treatment in Porcine Model Pebax with shockwave balloon catheter coated with Formulation 1 were tracked and placed at the site of inflation in porcine femoral arteries (female farm pigs, Sus scrofa domestica), and inflated to a balloon-to-artery diameter ratio of ~1.20. The Pebax with shockwave balloon catheter were inflated, and a simulated lithotripsy treatment consisting of a 1 minute-long acoustic shock sequence were performed during the drug transfer period. At the end of the shock sequence, the PTA was deflated, tracked to a second location and inflated and a second 1 minute-long mock lithotripsy treatment was performed. At the end of the second shock sequence, the PTA was deflated and removed from the animal. Each animal was given ASA (0.081 g) and Clopidogrel (0.075 g) by mouth daily for three days prior to treatment, and was fasted overnight before the procedure. For surgical procedures, after sedation a marginal ear vein was cannulated for infusion of intravenous fluids and medications. The animal was intubated for administration of anesthetic gases and placed on the catheterization table. Under sterile conditions, a vascular introducer sheath was placed in the right carotid artery by surgical cut down. Continuous hemodynamic and electrocardiographic monitoring was maintained throughout the procedure. Using the guide catheter and or the marker guidewire as a calibration reference, the diameter of the vessel at reference sites proximal and distal to the intended site of implant, as well as the target site diameter, was measured. The remaining coating on the balloon catheter after the procedure was extracted with appropriate solvent and PTX quantified by RP-HPLC with benzonitrile as the internal standard. The % PTX remaining on the balloons was for 53% the Pebax balloon post first lithotripsy treatment, and 24% post 2nd lithotripsy treatment (see FIG. 11). PTX retained on the balloon is available for further treatment.

EXAMPLE 21

Figure 12:
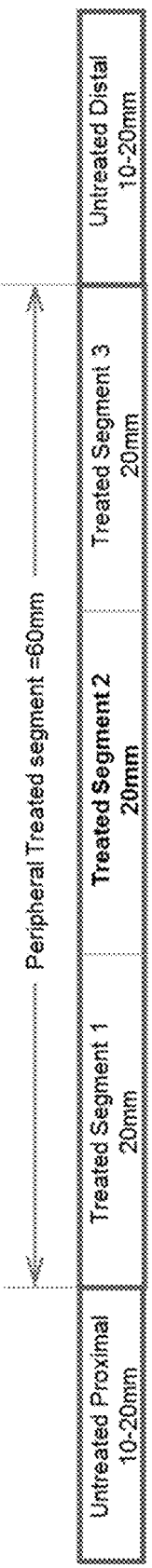
FIG. 12 is a graph depicting the segmentation of balloon treated vessel during necropsy as described in Example 21.

PK Study in Porcine Model 60 mm long Nylon 12, Pebax, and Pebax with shockwave balloon catheters coated with Formulation 1 were inflated in porcine peripheral arteries similar to example 17 at a balloon overstretch ratio of ~20%. Animals were sacrificed at specified time point (7d) and target vessels harvested. The treated vessel (60 mm) was cut into 3 treated segments and analyzed separately. The proximal untreated tissue and the distal untreated tissue are also harvested (FIG. 12). The concentration of PTX were measured in the vessels using a liquid chromatography-tandem mass spectrometry (LC-MS/MS) assay. The peak segment PTX concentration is reported for each vessel (i.e. peak PTX concentration in segements 1-3) (μg PTX/g vessel): Nylon 12, 7d=0.1-172.8; Pebax, 7d=0.1-40.3; Pebax with shockwave $1^{st}$ treatment site, 7d=2.1-290.3; Pebax with shockwave $2^{nd}$ treatment site, 7d=1.6-159.9.

EXAMPLE 22

Safety Study in Porcine Model

Coated Nylon 12 balloon catheter with Formulation 1 were inflated in porcine peripheral arteries similar to Example 21. Uncoated balloon (POBA) were used as controls and inflated in the similar fasion. At termination seven days after balloon inflation, the animals were euthanized, the downstream skeletal muscles and main organs was excised and examined for any abnormalities, and the vasculature was perfused with lactated Ringer's solution, then neutral buffered formalin and processed for histology. Artery segments were embedded in paraffin, sectioned (approximately 5 µm) and stained with hematoxylin and eosin (H&E) and Movat stain. Analysis by the study pathologist included semi-quantitative and descriptive histopathology and Histomorphometry. Higher fibrin and smooth muscle cell loss score of Formulation 1 indicated drug effect in tissue, otherwise, no significant differences in histology or Histomorphometry scores were noted between Formulation 1 and POBA.

EXAMPLE 23

Preclinical Study in Porcine Model

A swine model was chosen for preclinical trials. Pigs were used because it had been extensively used for stent and angioplasty studies, resulting in a large volume of data on the vascular response properties and its correlation to human vascular response. These studies are conducted in vivo, as there are no suitable in vitro models that can mimic the complex biological responses to balloon angioplasty.

The porcine and human arteries have correlatively similar anatomy and the porcine model is recommended for use in preclinical studies by the FDA and Schwartz et al., *Circulation.* 106:1867-1873 (2002).

Sus scrofa pigs were used in these studies. The animals were at least 10 weeks old, non-diseased, and all female or castrated. Each animal used in the study was attributed a study number and tagged by an ear tag at angioplasty. For the blank animal, an ear tag was prepared but not installed. The protocol was reviewed and approved by the CIPAA for compliance with the Canadian Council on Animal Care regulations prior to study initiation.

Procedures

To prevent or reduce occurrence of thrombotic events, animals were administered oral acetylsalicylic acid (325 mg) and clopidogrel (300 mg initial dose, 75 mg subsequently) at least three days prior to intervention and continuing until sacrifice. The drugs were crushed to powder and mixed with food; therefore, treatment was not administered when animals were fasted.

Animals were fasted prior to anesthesia and were anesthetized with ketamine, azaperone, and atropine or ketamine, acepromazine, and atropine administered intramuscularly (IM). Anesthesia induction or tracheal intubation was achieved with propofol injected intravenously (IV) via a catheter in a vessel of the left or right ear. Upon induction of anesthesia, the subject animal was intubated and supported with mechanical ventilation. Isoflurane in oxygen was administered to maintain a surgical plane of anesthesia.

In the K12 study described below, animals were injected IM with one dose of antiobitic Excede® (ceftiofur) to prevent postoperative infections. Torbugesic® (butorphanol) was administered IM to prevent pain sensitization and minimize postoperative pain. Rimadyl® (carprofen, 3 mg/kg, PO) was also administered as a postoperative analgesic on day 1.

In the K13 study described below, animals were injected IM with long action penicillin (Duplocillin®, ProPen LA, Penpro or similar). Buprenophine HCl (Vetergesic) was administered IM was administered IM to prevent pain sensitization and minimize postoperative pain.

After induction of anesthesia, the left or right femoral artery was accessed through an incision made in the inguinal region. An arterial sheath was introduced and advanced into the artery. For local anesthesia, Bupivacain 0.25% was infiltrated and/or locally dropped into the surgical site. An initial heparin bolus was administered and activated clotting time (ACT) was measured at least every 30 minutes and recorded. If ACT was <300 seconds, additional heparin was administered.

Blood samples of at least 3 mL in each tube were obtained from all animals during the procedures (when the animal was under anesthesia) before treatment and prior to termination. For the blank, at least 200 mL blood was collected and centrifuged to generate about 100 mL plasma. No blood samples was collected from the LIT animal. Samples were centrifuged as per Testing Facility SOP within approximately 1 hour of collection. Plasma was harvested and was kept on dry ice pending storage in a −80° C. freezer pending shipment to the Analytical Chemistry Site. The blood sample harvested from the blank animal was performed after appropriate sedation after propofol administration.

After treatment, animals were euthanized by inducing or maintaining deep anesthesia, followed by a lethal injection of saturated potassium chloride (KCl, rapid IV bolus). Death was confirmed by observation of ventricular fibrillation on the ECG.

Vessel Angiography

An initial angiography was performed prior to treatment. Under fluoroscopic guidance, a guide catheter was inserted through the sheath and advanced to the appropriate location. After placement of the guide catheter, nitroglycerin was delivered intraarterially to achieve arterial vasodilatation and angiographic images of the vessel were obtained with contrast media to identify the proper location for treatment site (designated pre-treatment angiography). A segment of artery was chosen, when possible, close to bifurcation or other markers, and measurements were performed up to the ostium to facilitate the site location at harvest. A guidewire was inserted into the chosen artery. Quantitative Vessel Angiography (QVA) was performed at this time to document the reference diameter for balloon angioplasty. Proximal and distal reference diameter was noted.

A final angiography was also performed after treatment. After induction of anesthesia, the artery of interest was accessed through an incision made in the inguinal region or a percutaneous access was used for some animals. Nitroglycerin was delivered to the treated arteries to achieve vasodilatation and QCA image capture was performed for each treated site using fluoroscopy. Each treated artery was qualitatively evaluated for lumen narrowing (treated and proximal/distal non-treated segments), dissection, thrombosis, and aneurysm.

The fluoroscopic output from the treated site (pre-treatment, balloon and post-treatment angiography) and at explantation (final angiography) were recorded in digital format. A single image was selected of the treated area; from this image, QVA measurements were obtained using Medis QCA-CMS 6.0 or QAngio® XA 7.3 (or higher) system. Parameters measured or calculated included:

Mean lumen diameter (or "lesion" on the Medis software reports) of the treated region (balloon, post-treatment, and final angiographies) or corresponding artery region (pre-treatment angiography).

Minimal lumen diameter (MLD, or "obstruction" on the Medis software reports) of the treated region (post-treatment and final angiographies only).

Diameter stenosis [1−(MLD/RVD)]×100] where RVD is a calculation of the reference diameter at the position of the obstruction (measure obtained by a software-based iterative linear regression technique to generate an interpolation of a projected vessel without the lesion) (final angiographies only).

Balloon to artery ratio [balloon/pre-implantation mean luminal diameter].

Late loss [post-implantation MLD-final MLD]

Balloon Angioplasty The balloon was introduced into the artery by advancing the balloon catheter through the guide catheter and over the guide wire to the delivery site. It was deployed to achieve balloon-to-artery ratio of 1.20:1 (based on treated vessel segment) with a range of 1.15:1 to 1.3:1 for at least 60 seconds to allow sufficient time for transfer of the therapeutic balloon coating to the vessel wall, after which vacuum was applied to the inflation device in order to deflate the balloon. Complete balloon deflation was verified with fluoroscopy (designated post-balloon angiography). Blood perfusion was evaluated using Peripheral Arterial Flow (PERI) grading or TIMI (Thrombolysis In Myocardial Infarction) flow grading; presence of major side branches and/or tortuosity was noted. Balloon angioplasty was repeated in the other vessel sites until the target treatment number was reached. After treatment, all balloons were kept in an appropriate vial (on dry ice or in a −80° C. freezer) for analysis. In cases when necessary, lidocaine was administered to treat cases of arrhythmia, nitroglycerin was administered to treat cases of arterial vasospasms, and atropine sulfate was administered to treat bradycardia. No additional drugs were administered during the implantation procedures.

Necropsy

K12 Study—All treated animals surviving to scheduled termination were subjected to a comprehensive necropsy, defined as gross examination of the heart and treated vessels, the whole body (external surface), all orifices, thoracic and abdominal cavities, and their contents. Lesions found during necropsy procedures/tissue collection were documented and collected when feasible, immersion-fixed in neutral buffered formalin (NBF) and processed for histology. Untreated sites proximal and distal to the treated site, as well as the myocardium downstream to the treated site, were also harvested for analysis. All treated sites were used for pharmacokinetic analysis. Hearts were perfused with lactated Ringer's solution (LRS), then NBF and immersed in NBF with the animal's ear tag until processed for histology. In addition to the animals that were treated, the blank animal was used as a control for blood and tissue analysis. LAD, LCx, and RCA vessels were harvested. Hearts were opened and then immersed in NBF with the animal's ear tag until possible processing for histology. Portions of the distal myocardium from the blank animal were also harvested from the LAD, LCx, and RCA. A gross examination of this animal was performed in order to assess any genetic abnormalities, such as cysts, that may have been present in the trial animals.

K13 study—In addition to the procedures described above, the skeletal muscle on each leg was grossly examined. Samples were collected in the center of the muscle, immersion-fixed in neutral buffered formalin (NBF) pending possible histology. Coronary band (hoof) samples downstream from the external or internal femoral arteries were collected for each leg, and stored in NBF pending possible analysis. The blank animal was again used as a control for blood and tissue analysis. LAD, LCx, RCA, right and left internal iliac arteries, and SFA/PFA vessels were harvested. The skeletal muscle and coronary band samples downstream from the external or internal femoral arteries were also collected.

Statistical Analyses

Selected values are expressed as mean±standard deviation. Statistical evaluation of possible differences between groups in selected QCA and histopathologic measurements was performed using Sigma Plot software. All Test and Control Articles were compared at 28D. A value of $p<0.05$ was considered statistically significant.

For continuous data, equal variance and normality tests were initially performed. When both were successful, One Way Analysis of Variance (ANOVA) was used (with Tukey's post-hoc tests for multiple comparisons). When either equal variance or normality tests failed, Kruskal-Wallis (ranks with Dunn's method) was conducted to compare groups.

For the histologic ordinal scores, the Kruskal-Wallis test (with Dunn's method for post-hoc group comparisons) was performed.

Preclinical Study K12

The objective of the study was to determine the amount of drug delivered from the drug-coated balloons (DCBs) and retained after 28 days in the arterial wall and surrounding tissue of porince (Sus scrofa) coronary arteries. A total of 22 animals were used; for histology: n=8; for PK: n=12; blank: n=1, and lost in transit (LIT): n=1.

There were five groups in this study. The three test articles were paclitaxel-containing drug-coated balloon formulations with Formulation 1, Formulation 3, and Formulation 4. As controls, uncoated balloons or Biotronik® Pantera Lux were used. 3.0 mm×20.0 mm balloons were used. In each pig, treatments were performed in the three main coronary arteries: left anterior descending coronary artery (LAD), left circumflex coronary artery (LCx), and right coronary artery (RCA). One balloon type was used per each pig.

All animals survived to 28 days with no notable clinical observations. Aneurysm, dissection, thrombosis, and lumen narrowing in the proximal or distal marginal vessel were not observed at terminal angiography in all animals. Lumen narrowing in the treated segment was observed in 15/60 treated arteries, and blood flow in all arteries was rated as complete (flow grade of 3). As a result of the study, the RVD, overstretch, late loss, and diameter stenosis are summarized below in Table 1.

TABLE 1

| | Results of study | | | | |
|---|---|---|---|---|---|
| Parameter | Uncoated n = 4 | Formulation 1 n = 14 | Formulation 3 n = 14 | Formulation 4 n = 14 | Pantera Lux n = 14 |
| RVD (mm) | 2.59 ± 0.19 | 2.50 ± 0.21 | 2.61 ± 0.35 | 2.56 ± 0.29 | 2.56 ± 0.31 |
| Overstretch | 1.24 ± 0.03 | 1.23 ± 0.04 | 1.22 ± 0.04 | 1.21 ± 0.04 | 1.19 ± 0.03 |

TABLE 1-continued

Results of study

| Parameter | Uncoated n = 4 | Formulation 1 n = 14 | Formulation 3 n = 14 | Formulation 4 n = 14 | Pantera Lux n = 14 |
|---|---|---|---|---|---|
| Late loss (mm) | 0.05 ± 0.09 | 0.06 ± 0.13 | 0.11 ± 0.23 | 0.01 ± 0.03 | 0.06 ± 0.15 |
| Diameter stenosis (%) | 15.13 ± 5.60 | 11.74 ± 7.64 | 11.35 ± 6.60 | 6.59 ± 5.55 | 14.32 ± 7.17 |

Figure 13:
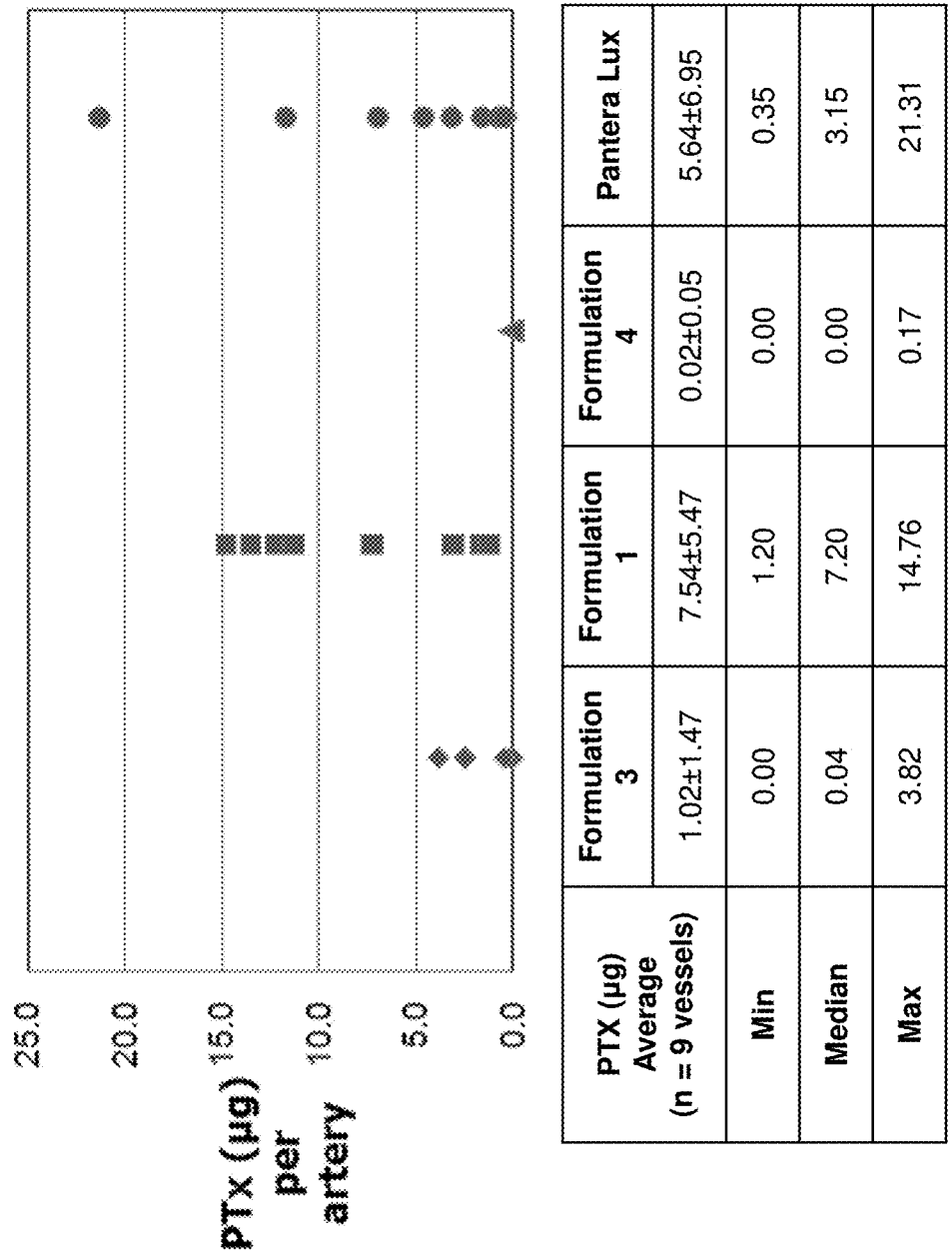
FIG. 13 is a graph depicting the median level of paclitaxel (PTX) in vessels following treatment with different coatings as described in Example 23. The median level of paclitaxel (PTX) in vessels treated with Formulation 1 (7.2 µg PTX/g of vessel) were double that of Pantera Lux (3.15 µg PTX/g of vessel), while the median level of PTX observed for Formulation 3 (0.04 µg PTX/g of vessel) and Formulation 4 (<0.01 µg PTX/g of vessel) delivered the lowest median levels of PTX to vessels.
Figure 14:
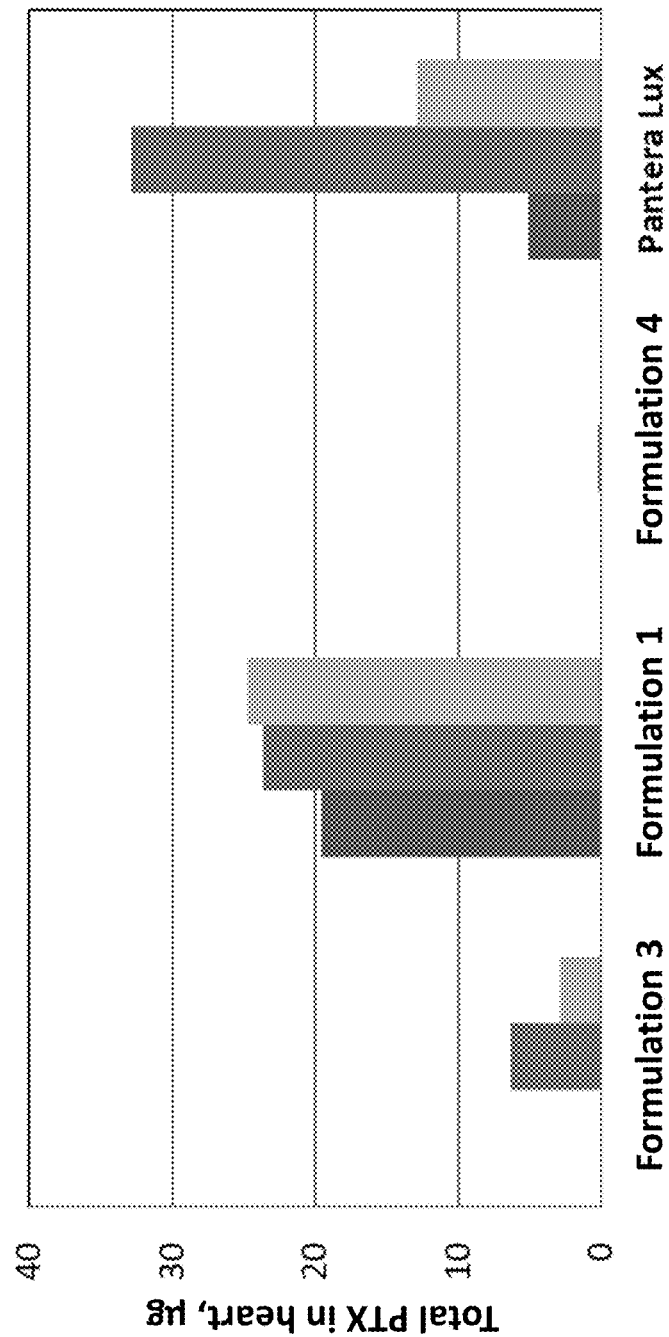
FIG. 14 is a graph depicting the amount of paclitaxel (PTX) delivered to the heart of in a porcine study as described in Example 23. It was observed that PTX was delivered at a consistently high dose to Formulation 1-treated hearts in comparison to other formulations. Each bar of the graph represents a given heart; there were three total hearts per group.

It was observed that the median level of paclitaxel (PTX) in vessels treated with Formulation 1 (7.2 µg PTX/g of vessel) were double that of Pantera Lux (3.15 µg PTX/g of vessel), while the median level of PTX observed for Formulation 3 (0.04 µg PTX/g of vessel) and Formulation 4 (<0.01 µg PTX/g of vessel) delivered the lowest median levels of PTX to vessels (see FIG. 13). For the two formulations that delivered the largest amounts of PTX to the vessel, lower levels of PTX were observed in the distal myocardium with Formulation 1 (average=0.03±0.06) relative to Pantera Lux (0.33±0.64). It was also observed that PTX was delivered at a consistently high dose to Formulation 1-treated hearts, as shown in FIG. 14.

The consistency of Formulation 1 PTX delivery was observed across each individual animal, shown in Table 2, as well as across each vessel type, shown in Table 3.

TABLE 2

Delivery of PTX across each individual animal

| Average PTX (µg PTX/g of vessel) | Formulation 1 | Formulation 3 | Formulation 4 | Pantera Lux |
|---|---|---|---|---|
| Animal 1 (n = 3) | 6.51 ± 6.05 | 0.00 ± 0.00 | 0.01 ± 0.01 | 1.70 ± 1.40 |
| Animal 2 (n = 3) | 7.87 ± 6.58 | 2.10 ± 1.91 | 0.06 ± 0.10 | 10.94 ± 9.05 |
| Animal 3 (n = 3) | 8.23 ± 6.11 | 0.95 ± 1.31 | 0.01 ± 0.01 | 4.29 ± 6.42 |

TABLE 3

Delivery of PTX across each vessel type

| Average PTX (µg/ vessel type) | Formulation 1 | Formulation 3 | Formulation 4 | Pantera Lux |
|---|---|---|---|---|
| RCA (n = 3) | 9.99 ± 3.63 | 1.63 ± 0.65 | 0.06 ± 0.03 | 3.08 ± 1.36 |
| LAD (n = 3) | 5.33 ± 2.24 | 1.27 ± 0.73 | 0.02 ± 0.01 | 2.73 ± 1.05 |
| LCX (n = 3) | 7.30 ± 2.95 | 0.15 ± 0.08 | 0.00 ± 0.00 | 11.12 ± 4.68 |

Preclinical Study K13

A second study was performed to assess the safety of Formulation 1-coated PTA balloons according to the procedures described above. Four balloons (5.0×40.0 mm) were used in this experiment: Formulation 1-coated percutaneous transluminal coronary angioplasty (PTCA), compared to Biotronik® Pantera Lux, and Formulation 1-coated percutaneous transluminal angioplasty (PTA) compared to Medtronic® IN.PACT™.

Treatments were performed either in the peripheral or coronary arteries. For PTCA, treatment was performed in the three main coronary arteries: left anterior descending coronary artery (LAD), left circumflex coronary artery (LCx), and right coronary artery (RCA). For PTA, treatments were performed in the superficial femoral arteries (SFAs) and profunda femoris arteries (PFAs). One balloon type was used per each pig Pharmacokinetic results for peripheral and coronary artery samples are summarized below in Table 4. Overall, the coronary artery tissue PK data from confirms the high level of PTX delivery to the vessel wall from Formulation 1-coated balloons, and the observed drop in tissue drug concentration between 7 days (K13 study) and 28 d (K12 study) for Formulation 1-treated arteries is consistent with literature data for commercial DCBs.

TABLE 4

PK results for peripheral and coronary arteries, by test group.

| Test Group | Description | PTX at 7 d (µg/g) | PTX at 28 d from K12 study (µg/g) |
|---|---|---|---|
| Coronary arteries | | | |
| Formulation 1-HT PTCA | Formulation 1 (80:20, 3.0 µg/m² PTX) on QualiMed 3 × 20 mm, Hemoteq-coated | 104.1 ± 59.8 n = 3 | 37.5 ± 26.7 n = 9 |
| Pantera Lux | Biotronik ® Pantera Lux 3 × 20 mm (BTHC excipient, 3.0 µg/m² PTX) | 31.1 ± 23.0 n = 3 | 24.5 ± 23.4 n = 8 |
| Peripheral arteries | | | |
| Formulation 1-HT PTA | Formulation 1 (80:20, 3.0 µg/m² PTX) on QualiMed 5 × 40 mm, Hemoteq-coated | 1.02 (0.74, 1.30) n = 2 | N/A |
| IN.PACT ™ | Medtronic IN.PACT ™ Admiral ™ 5 × 40 mm (urea excipient, 3.5 µg/m² PTX) | 5.45 (4.87, 6.02) n = 2 | N/A |

While Formulation 1-treated peripheral arteries show lower PTX retention than those treated with the IN.PACT™ control, the drug tissue level for Formulation 1-treated arteries at 7 days is within the range of clinically proven devices such as Lutonix (Bard) (1.0±0.9 µg/g 7 d after treatment with Lutonix balloons) (Yazdani et al., *Catheterization and Cardiovascular Interventions.* 83:132-140 (2014)). This pilot study was conducted with minimal coating optimization pre-work. As detailed in Table 4, analysis supports the potential for increased PTX uptake/retention for Formulation 1-coated balloons (near the level of In.Pact) by optimizing the coating morphology to provide full balloon surface coverage. Data from this study clearly support both high PTX transfer to coronary artery walls as well as the viability of the Formulation 1 balloon coating for peripheral artery applications. At 7 days after treatment, Formulation 1-treated coronary arteries show PTX tissue concentrations of about 104 µg/g, a high value that is consistent with the 38 µg/g concentration observed at 28 days in the previous study described in study K12.

EXAMPLE 24

Preparation of Formulation 5

Compound 1 and sirolimus were dissolved at 20:80 w/w ratio in heptane:ethyl acetate (50:50 v/v ratio) and both solutions were used immediately. Solutions were drop casted onto Nylon 12 coupons and visually inspected.

EXAMPLE 25

Preparation of Formulation 6

Compound 1 and sirolimus were dissolved at at 95:5 w/w ratio in heptane:ethyl acetate (50:50 v/v ratio) and both solutions were used immediately. Solutions were drop casted onto Nylon 12 coupons and visually inspected.

EXAMPLE 26

Preparation of Formulation 7

Compound 1 and sirolimus were dissolved at 90:10 w/w ratio in heptane:tetrahydrofuran:methanol (72.5:22.5:5 v/v/v ratio) and used immediately. Solutions were applied onto Nylon 12 tubing using an drop-and-drag coater and visually inspected. Examples at local drug density of 1.6 and 4 µg/mm$^2$ were prepared. The features observed with the drop-casting and drop-and-drag coating methods were consistent. A crystalline sirolimus drug polymorph was confirmed by DSC analysis of material obtained after evaporation of the solvents: $T_m$=180° C.

EXAMPLE 27

Preparation of Formulation 8

Compound 2 and sirolimus were dissolved at 20:80 w/w ratio in heptane:ethyl acetate (50:50 v/v ratio) and used immediately. Solutions were drop casted onto Nylon 12 coupons and visually inspected. As compared to the Formulation 5 (Example 24), a lower crystal coverage was observed, as evidenced by the more prominent clear coating areas.

EXAMPLE 28

Exposure of Coating in Phosphate Buffered Saline Solution (PBS)

Formulation 5 and Formulation 8 coated Nylon 12 coupon were immersed into phosphate buffered saline solution for 2 minutes. Formulation 5 remained intact, while Formulation 8 exhibited significant particle shedding.

EXAMPLE 29

Preparation of Cryo-Milled Sirolimus and Characterization 1 to 1.5 g of sirolimus (crystalline, purchased from LC Laboratories®) was milled into micron-sized particles using a CryoMill (Retsch®) at −196° C., 30 Hz for 15 min. The crystalline sirolimus drug polymorph was preserved and confirmed by X-ray powder diffraction (XRD) analysis and DSC. $T_m$=180° C.

EXAMPLE 30

Preparation of Formulation 9

Cyro-milled sirolimus from Example 29 was suspended in methyl tert-butyl ether (MTBE) with dissolved Compound 1 (range from 50:50 to 95:5 w/w) with varying sirolimus concentration (20-120 mg/mL) and used while stirring. Suspensions were drop casted onto Nylon 12 coupons and visually inspected. It was noted that the higher the sirolimus concentration, the more crystalline the coating.

Closer inspection of Formulation 9 coatings under SEM indicates that sirolimus concentrations greater than 80 mg/mL are substantially crystalline, as no clear evidence of amorphous morphological features was found during imaging. Formulation 9, therefore, yields coatings of varying degrees of sirolimus crystallinity depending on concentration. Specifically, solutions of a concentration 80 mg/mL can be used to prepare highly crystalline reference samples of Formulation 9 (crystalline control). % crystallinity of the crystalline control as measured by PXRD: 92%.

EXAMPLE 31

Preparation of Formulation 10

Compound 1 and sirolimus were dissolved in tetrahydrofuran (THF) or acetone in proportions ranging from 50:50 to 95:5 w/w and a sirolimus concentration range from 20-200 mg/mL. Solutions were drop casted onto Nylon 12 coupons and visually inspected. The resulting coatings were colourless and transparent, consistent with amorphous sirolimus; results were equivalent with either THF or acetone solvents. The absence of Bragg peaks seen in the XRD analyses confirmed the amorphous nature of the material.

Formulation 10 in THF was coated onto 3.0×20 mm Nylon 12 percutaneous transluminal coronary angioplasty (PTCA) balloon catheters and 5.0×60 mm Nylon 12 percutaneous transluminal angioplasty (PTA) balloon catheters by a drop-and-drag coating method and dried overnight to form coatings containing varying sirolimus loading (3.0-7.0 µg/mm$^2$). The same colourless and transparent coating characteristics noted for Nylon 12 coupons were also observed on coated balloons.

EXAMPLE 32

Balloon Coating of Formulation 9 and Characterization

Figure 15:
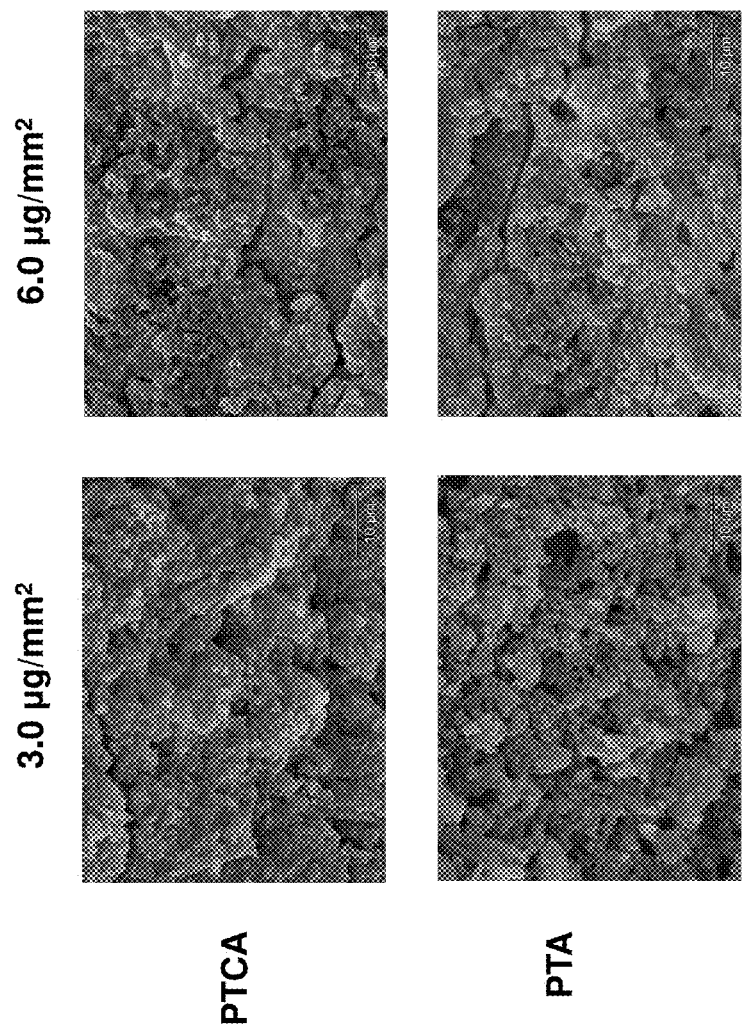
FIG. 15 are a series of SEM images of Formulation 9 coated PTCA and PTA balloon catheters.

Formulation 9 was coated onto 3.0×20 mm Nylon 12 percutaneous transluminal coronary angioplasty (PTCA) balloon catheters and 5.0×60 mm Nylon 12 percutaneous transluminal angioplasty (PTA) balloon catheters by a drop-and-drag coating method and dried overnight to form coatings containing varying sirolimus loading (3.0-7.0 µg/mm$^2$). SEM images of all coated balloons displayed the expected crystalline drug morphology (see FIG. 15).

EXAMPLE 33

Balloon Process Conditions and Characterization

Figure 16:
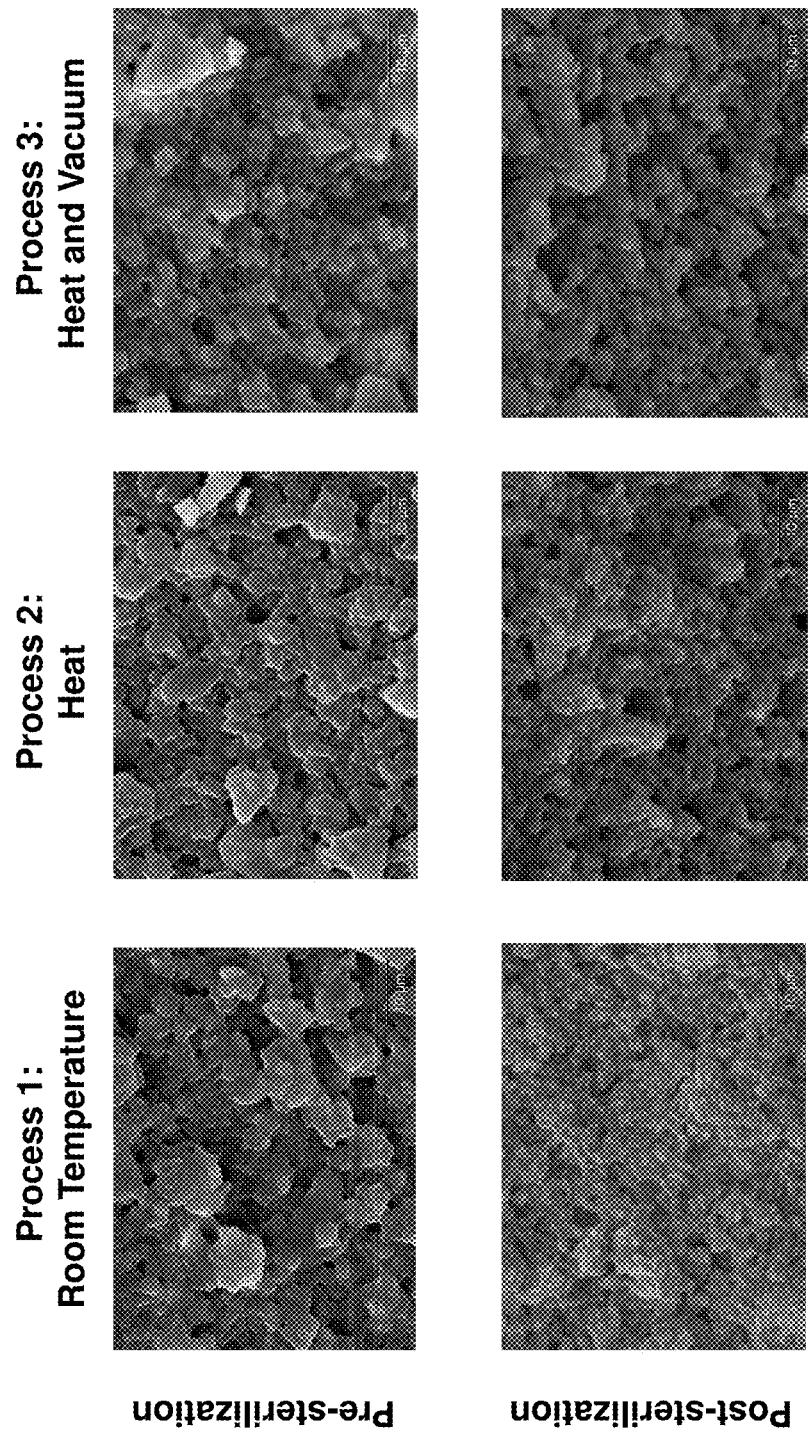
FIG. 16 are a series of SEM images of Formulation 9 coated PTCA balloon catheters subject to various drying processes immediately after coating.

PTCA balloon catheters were coated with Formulation 9 as in Example 32 and subjected to various drying processes immediately after coating: Process 1: room temperature overnight; Process 2: heat (50° C.) for 1 to 5 days; Process 3: heat (50° C.) and vacuum for 1 to 5 days. All coated balloons were then sterilized by EtO. SEM images of all coated balloons displayed the expected crystalline drug morphology. Process 2 and Process 3 balloon coatings showed fewer morphological changes post-sterilization suggesting bulk removal of solvent (FIG. 16). Residual MTBE solvent: Process 1 pre-sterilization 59120 ppm, post-sterilization 12810 ppm; Process 2 pre-sterilization 7910 ppm, post-sterilization 2011 ppm; Process 3 pre-sterilization 2104 ppm, post-sterilization 400 ppm.

EXAMPLE 34

Coupon Release in PBS Tween Buffer

Figure 17:
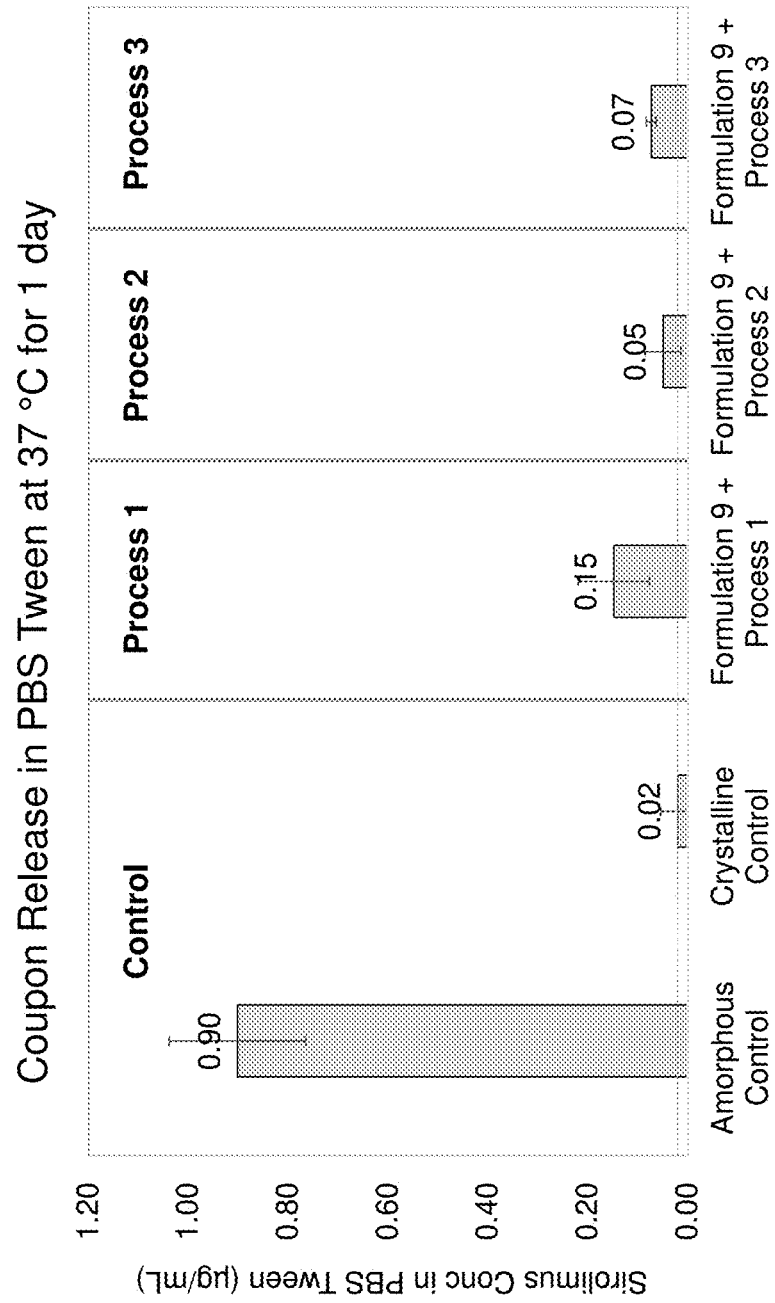
FIG. 17 is a graph depicting sirolimus release in PBS tween buffer of Formulation 9 from Nylon 12 coupons after 24 hours.

Formulation 9, Formulation 10 (amorphous control), and a suspension of Compound 1 with 80 mg/mL sirolimus (crystalline control, as described in Example 30) were drop-casted onto Nylon 12 coupons and dried as in Example 33. Nylon 12 coupons were immersed in 40 mL of PBS tween buffer and placed in a shaker at 37° C. for 24 hours. Buffer exchanges were performed at 1 hour and 2 hours to remove loose particles. At 24 hours, PBS tween was removed from the container, and the concentration of sirolimus release in PBS tween buffer was directly quantified using RP-HPLC (FIG. 17). The remaining sirolimus on coupon was measured by dissolving the coating in acetonitrile and quantified using RP-HPLC. Nylon 12 coupons of Formulation 9 dried with Process 2 and 3 had similar sirolimus release to the crystalline control, suggesting that these coatings were substantially crystalline and would have longer retention in vivo compared to amorphous coatings (Formulation 10) due to lower solubility.

EXAMPLE 35

Balloon Release

PTCA balloon catheters were coated and dried in a similar fashion as Example 34. After EtO sterilization, balloons were immersed in 40 mL of PBS tween buffer and placed in a shaker at 37° C. for 24 hours. Buffer exchanges were performed at 1 hour and 2 hours to remove loose particles. At 24 hours, PBS tween was removed from the container, and the concentration of sirolimus release in PBS tween buffer was directly quantified using RP-HPLC. The remaining sirolimus on PTCA balloon catheters was measured by dissolving the coating in acetonitrile and quantified using RP-HPLC.

24 h Sirolimus release post sterilization (µg/mL): Formulation 9+Process 1, 0.42 µg/mL; Formulation 9+Process 2, 0.39 µg/mL; Formulation 9+Process 3, 0.42 µg/mL; crystalline control, 0.37 µg/mL; and amorphous control, 2.29 µg/mL. These results suggest that balloons coated with Formulation 9 were substantially crystalline and would have longer retention in vivo compared to amorphous coatings (Formulation 10) due to lower solubility.

EXAMPLE 36

Bioactivity of Released Sirolimus

Formulation 7 and Formulation 9, each at a sirolimus-to-Compound 1 ratio of 80:20 w/w, were drop-casted onto Nylon 12 coupons and sterilized by EtO. Corresponding sirolimus-only control samples were prepared at the same concentrations and in the same solvent systems as Formulation 7 and Formulation 9 by drop-casting onto Nylon 12 coupons, and then sterilized by EtO. Under sterile conditions, the Nylon 12 coupons were immersed in Dulbecco's Modified Eagle Medium (DMEM) and placed in a shaker at 37° C. for 5 hours towards a target concentration >20 ng/mL of released sirolimus. Concentrations in DMEM were directly quantified using RP-HPLC, then adjusted to 20 ng/mL by dilution with DMEM and Fetal Bovine Serum (FBS, 10% overall content). An additional control sample for sirolimus at the same concentration (20 ng/mL) was prepared by spiking an acetone solution directly into cell culture media (DMEM with 10% FBS). Sterile conditions were ensured by filtration of the acetone stock solution through a syringe filter of 0.2 µm pore size.

The bioactivity of released sirolimus in cell culture media was evaluated using the WST-1 assay to assess cell growth inhibition. Rat Aortic Smooth Muscle Cells (RASMCs) were first seeded in two 96-well plates and cultured overnight. The growth media was removed by aspiration and exchanged with the drug release samples described above, each adjusted to 20 ng/mL. Metabolic activity was then measured after a growth period of 72 hours using an analytical wavelength of 450 nm, and a reference wavelength of 650 nm. Data were normalized against RASMCs grown in drug-free media, and compared against cell culture media spiked with sirolimus at 20 ng/mL, prepared as described above. Growth inhibition results were similar for all samples, which confirms that sirolimus released from a sterilized coating in the presence or absence of Compound 1 retains drug potency. These values were also equivalent to those of freshly-spiked culture media at the same concentration. Normalized cell growth at 72 hours: drug released from Formulation 7 coupon 0.338±0.016; drug released from sirolimus coupon prepared with Formulation 7 solvent system 0.329±0.035; drug released from Formulation 9 coupon 0.341±0.016; drug released from sirolimus coupon prepared with Formulation 9 solvent system 0.291±0.031; drug spiked directly into growth media 0.463±0.035.

EXAMPLE 37

Particle Size Analysis for Formulation 9

A suitable apparatus was used based on the principle of light-obscuration that allows for an automatic determination of the size of particles and the number of particles according to size. An environmental check was performed as per USP <788> to confirm suitability of the testing environment. The apparatus is calibrated using dispersions of spherical particles for known sizes between 10 mm to 150 mm. These standard particles were dispersed in particle-free water. Care was taken to avoid aggregation of particles during dispersion. USP41-NF36 S1 <788> was used as a guideline for sample testing.

Particle Size Analysis on PTCA Balloon Catheters

Phosphate buffered saline at 37° C. was filled through silicone tubing connections. A Nylon 12 PTCA balloon catheter coated with Formulation 9+Process 1 was tracked through the silicone tubing, then inflated to establish contact with silicone tubing. Once inflated, the balloon was held in place for 1 minute, and then deflated and removed from the tubing. Buffer after inflation was analyzed by a HIAC Liquid Particle Counter (MII B1616712). Noted that uncoated PTCA balloon catheters were used as control samples. The cumulative number of particles were measured for (i) Formulation 9 of 3 µg/mm² on 3×20 mm Nylon 12 PTCA balloon catheter (>10 µm: 7223; >25 µm: 777; >70 µm: 11) and (ii) for Formulation 9 of 6 µg/mm² on 3×20 mm Nylon 12 PTCA balloon catheter (>10 µm: 6027; >25 µm: 888; >70 µm: 10).

Particle Size Analysis Conclusions

The particle counts observed for Formulation 9 coated on Nylon 12 PTCA balloon catheters was significantly lower that the particle counts of coronary artery PTX competitors: 3.5×20 mm Minvasys PTX coated balloon catheter (>10 µm: 22730; >25 µm: 2326; >70 µm: 16, normalized to 3×20 mm balloon size), and 2.75×20 mm Minvasys PTX coated balloon catheter (>10 µm: 39989; >25 µm: 3712; >70 µm: 26, normalized to 3×20 mm balloon size), and 3×20 mm Pantera Lux® paclitaxel-eluting balloon (>10 µm: 108356; >25 µm: 13761; >70 µm: 63). Particle counts relative to crystalline sirolimus in Formulation 9 was not significantly differently from particle counts relative to the crystalline PTX in Formulation 1.

EXAMPLE 38

Assessment of Therapeutic Retention of Formulation 9 Balloon Coating Under Flow Conditions (Flow Loop Model)

Figure 18:
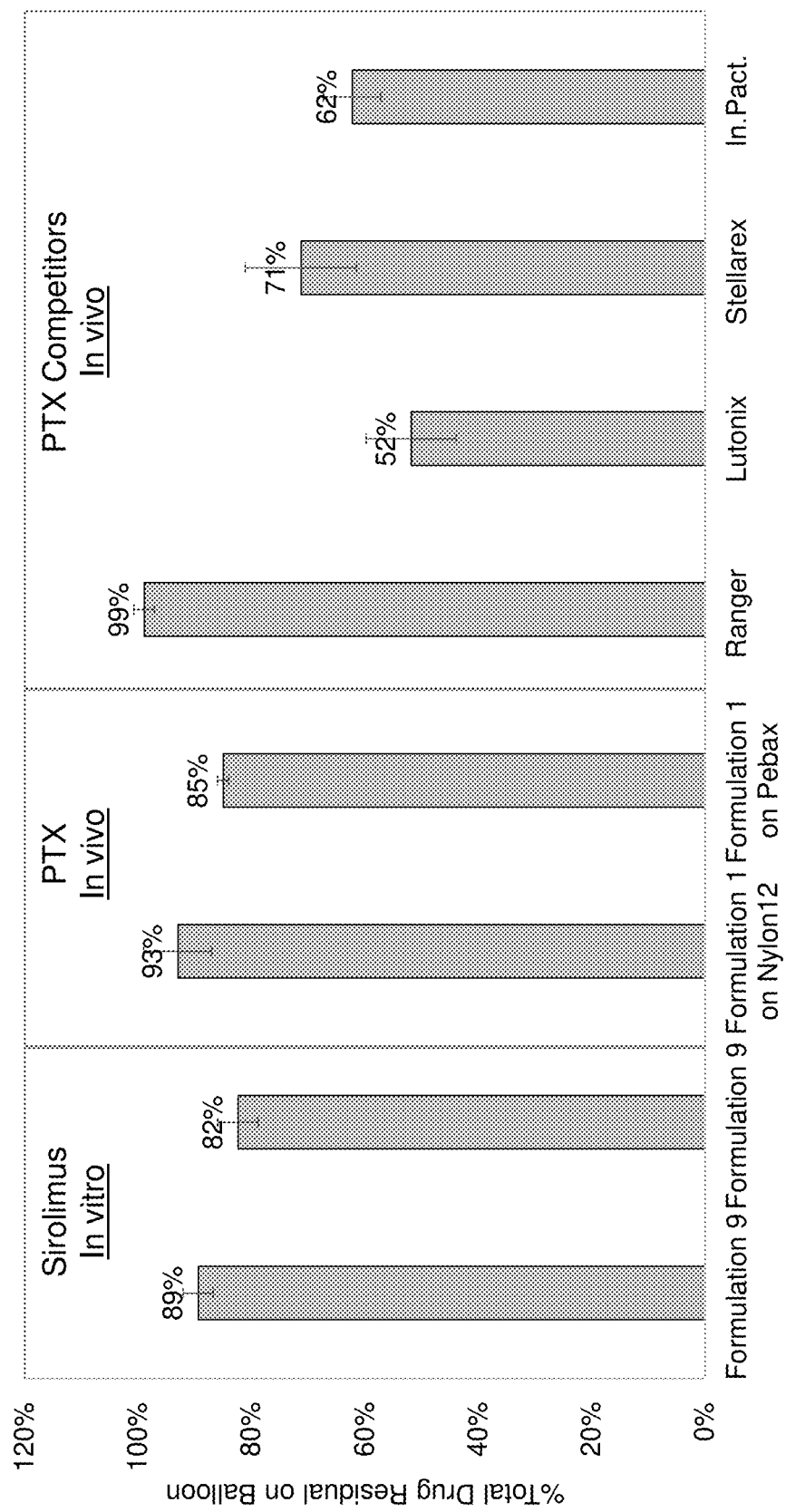
FIG. 18 is a graph depicting drug retention for Formulation 9 coated PTA balloon catheters compared to Formulation 1 coated Nylon 12 PTA balloon catheter, Formulation 1 coated Pebax PTA lithotripsy catheter, and competitor benchmarks Lutonix®, IN.PACT™, Ranger™, and Stellarex™

Phosphate buffered saline at 37° C. was pumped through silicone tubing connections. The pump flow rate was set similar to the rate of blood flow through femoral arteries (350 mL/min). A Nylon 12 PTA balloon catheter coated with Formulation 9+Process 2 was placed in the middle of the buffer flow for 2 minutes. The sirolimus remaining on the balloon catheter was measured by dissolving the coating in acetonitrile and quantified using RP-HPLC. The % sirolimus remaining was observed to be 89% for PTA containing 3.0 µg/mm² sirolimus and 82% for PTA containing 6.0 µg/mm² sirolimus. Sirolimus retention for Formulation 9 was higher than drug retention of PTX competitor benchmarks: Ranger, 99%, Lutonix, 52%, Stellarex, 71%, and In.Pact, 62% (see FIG. 18). The high retention of sirolimus observed for Formulation 9 was similar to the high retention of PTX observed for Formulation 1, 93% for Nylon 12 PTA balloon catheter coated with Formulation 1 and 85% for Pebax PTA lithotripsy catheter coated with Formulation 1 (see FIG. 18). This would suggest that a high percentarge of the sirolimus payload would be available at the target site and not reduced by transit-associated loss.

EXAMPLE 39

Assessment of Post-Treatment Retention of Formulation 9 Balloon Coating Under Flow Conditions (Flow Loop Model)

Phosphate buffered saline at 37° C. was pumped through silicone tubing connections. The pump flow rate was set similar to the rate of blood flow through femoral arteries (350 mL/min). A Nylon 12 PTCA balloon catheter coated with Formulation 9+Process 1 and Formulation 9+Process 2 was tracked through the silicone tubing under flow, then inflated to establish contact with silicone tubing. Once inflated, the balloon was held in place for 1 minute, and then deflated and removed from the tubing. The siroliums remaining on the balloon catheter was measured by stripping the coating and quantified using RP-HPLC.

Less drug retention was observed after sterilization for Formulation 9+Process 1 while drug residual on balloon was same pre and post sterilization for Formulation 9+Process 2. Process 2 improved consistency of performance post sterilization. Post treatment retention of Formulation 9 was within the range of the retention of Concept Medical Magic Touch® drug-eluting balloon: 39% and Nylon 12 PTCA coated with Formulation 1:58% (see FIG. 19).

EXAMPLE 40

PK Study in Coronary Artery Porcine Model 3.0 mm×20 mm Nylon 12 PTCA balloon catheter coated with Formulation 9+Process 2 at 3.0 and 6.0 µg/mm² were sterilized with EtO and inflated in porcine coronary arteries similar to Example 23 at a balloon overstretch ratio of ~20%. Concept Medical MagicTouch® DCB were used as controls.

Animals were sacrificed at a specified time point (29d) and target vessels harvested. The proximal untreated tissue and the distal untreated tissue were also harvested. The concentration of sirolimus was measured in the vessels using a liquid chromatography-tandem mass spectrometry (LC-MS/MS) assay; results are shown in Table 5.

TABLE 5

| Drug Coating | Sirolimus Content (µg/mm²) | Overstretch | Sirolimus Levels in Artery (µg/g) | Sample Size |
|---|---|---|---|---|
| Formulation 9 | 3.0 | 26 ± 5% | 0.83 ± 0.57 | 4 |
| Formulation 9 | 6.0 | 15 ± 3% | 7.98 ± 8.58 | 3 |
| Magic Touch | 1.3 | 15 ± 2% | 0.26 ± 0.33 | 2 |

EXAMPLE 41

Histopathology Study in Coronary Artery Porcine Model 3.0 mm×20 mm Nylon 12 balloon catheter coated with Formulation 9+Process 2 at 3.0 and 6.0 µg/mm² are sterilized with EtO and inflated in porcine coronary arteries similar to Example 40. Uncoated balloons (POBA) are used as controls and inflated in a similar fashion. At termination 28 days after balloon inflation, the animals are euthanized, the main organs are excised and examined for any abnormalities, and the heart is perfused with lactated Ringer's solution, then neutral buffered formalin and processed for histology. Artery segments are embedded in paraffin, sectioned (approximately 5 µm) and stained with hematoxylin and eosin (H&E) and Movat stain. Analysis by the study pathologist include semi-quantitative and descriptive histopathology and histomorphometry.

EXAMPLE 42

PK Study in Peripheral Artery Porcine Model 5.0 mm×60 mm Nylon 12 PTA balloon catheter coated with Formulation 9+Process 2 at 3.0 and 6.0 µg/mm² were sterilized with EtO and inflated in porcine peripheral arteries similar to Example 21 at a balloon overstretch ratio of ~12%. Animals were sacrificed at a specified time point (29d) and target vessels harvested. The treated vessel (60 mm) was cut into 3 treated segments (each segment: 20 mm length) that were analyzed separately. The proximal untreated tissue and the distal untreated tissue were also harvested. The concentration of sirolimus was measured in the vessels using a liquid chromatography-tandem mass spectrometry (LC-MS/MS) assay; results shown in Table 6 were calculated by taking the maximum value of the 3 treated segments.

TABLE 6

| Drug Coating | Sirolimus Content (µg/mm²) | Overstretch | Sirolimus Levels in Artery (µg/g) | Sample Size |
|---|---|---|---|---|
| Formulation 9 | 3.0 | 13 ± 5% | 0.44 ± 0.18 | 6 |
| Formulation 9 | 6.0 | 11 ± 4% | 1.17 ± 1.26 | 5 |

EXAMPLE 43

Assessment of Post-Treatment Retention of Balloon Coating in a Porcine Model

The remaining coating on the balloon catheter after the procedure in Examples 40-42 were extracted with appropriate solvent and sirolimus quantified by RP-HPLC. % sirolimus remaining on balloons: PTCA 3.0 µg/mm² 12%, PTCA 6.0 µg/mm² 10%, PTA 3.0 µg/mm² 30%, PTA 6.0 µg/mm² 19%, Concept Medical MagicTouch PTCA 20%.

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A coating comprising:
   (i) from 5% to 25% (w/w) of a compound of formula (I)

$$F_T-[B-(\text{oligo})]_n-B-F_T \quad \text{(I)},$$

wherein B is a hard segment formed from hexamethylene diisocyanate, oligo is an oligomeric segment including polytetramethylene oxide having a molecular weight of from about 800 Da to 1,500 Da, $F_T$ is a polyfluoroorgano group having the formula $(CF_3)(CF_2)_5CH_2CH_2O-$, and n is an integer from 1 to 10; and
   (ii) from 75% to 95% (w/w) sirolimus crystals.

2. The coating of claim 1, wherein said coating is a coating on at least a portion of a balloon catheter.

3. The coating of claim 1, wherein the coating comprises a sirolimus concentration of from 1.0 µg/mm² to 10.0 µg/mm².

4. The coating of claim 3, wherein the sirolimus concentration is 3.5±0.5 µg/mm².

5. The coating of claim 3, wherein the sirolimus concentration is 7.0±0.5 µg/mm².

6. A balloon catheter, wherein at least a portion of the surface of the balloon catheter comprises a coating of claim 1.

7. The balloon catheter of claim 6, wherein the balloon catheter comprises an energy generating element.

8. The balloon catheter of claim 6, wherein the balloon catheter comprises an element that generates ultrasound, heat, electromagnetic, mechanical, or vibrational energy.

9. The balloon catheter of claim 8, wherein the balloon catheter comprises an ultrasound generating element.

10. The balloon catheter of claim 9, wherein the ultrasound generating element is a lithotripsy electrode.

* * * * *